(12) United States Patent
Izumimoto et al.

(10) Patent No.: US 8,470,845 B2
(45) Date of Patent: Jun. 25, 2013

(54) ANALGESIC AND METHODS OF TREATING PAIN

(75) Inventors: Naoki Izumimoto, Kamakura (JP);
Kuniaki Kawamura, Kamakura (JP);
Toshikazu Komagata, Kamakura (JP);
Tadatoshi Hashimoto, Osaka (JP);
Hiroshi Nagabukuro, Osaka (JP)

(73) Assignee: Toray Industries, Inc. (JP)

( * ) Notice: Subject to any disclaimer, the term of this patent is extended or adjusted under 35 U.S.C. 154(b) by 906 days.

(21) Appl. No.: 11/667,136

(22) PCT Filed: Nov. 4, 2005

(86) PCT No.: PCT/JP2005/020297
§ 371 (c)(1),
(2), (4) Date: May 4, 2007

(87) PCT Pub. No.: WO2006/049248
PCT Pub. Date: May 11, 2006

(65) Prior Publication Data
US 2007/0299100 A1  Dec. 27, 2007

(30) Foreign Application Priority Data
Nov. 4, 2004 (JP) ................... 2004-320583

(51) Int. Cl.
*A61K 31/44* (2006.01)
*C07D 221/22* (2006.01)

(52) U.S. Cl.
USPC .......................... 514/289; 546/46

(58) Field of Classification Search
USPC ........................... 514/289; 546/74
See application file for complete search history.

(56) References Cited

U.S. PATENT DOCUMENTS
3,318,886 A    5/1967  Brown et al.
6,476,044 B1 *  11/2002  Wnendt et al. ............. 514/282
(Continued)

FOREIGN PATENT DOCUMENTS
EP   0 663 401 A1   7/1995
EP     846694 A1 *  6/1998
(Continued)

OTHER PUBLICATIONS

Kohn et al., Selected aspects of the clinical pharmacology of visceral analgesics and gut motility modifying drugs in the horse, Journal of Veterinary Internal Medicine, vol. 2, No. 2, Apr.-Jun. 1988, pp. 85-91, Abstract.*

(Continued)

*Primary Examiner* — Lezah Roberts
*Assistant Examiner* — Nannette Holloman
(74) *Attorney, Agent, or Firm* — DLA Piper LLP (US)

(57) ABSTRACT

An analgesic which may be applied to wide variety of pain from various causes is disclosed. The analgesic comprises as an effective ingredient a specific morphinan derivative having a nitrogen containing heterocyclic group, such as compound 1:

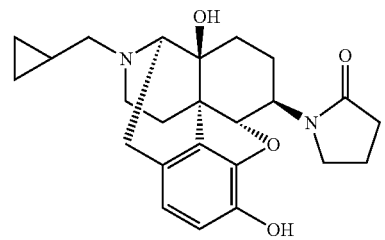

5 Claims, 8 Drawing Sheets

U.S. PATENT DOCUMENTS

| | | | |
|---|---|---|---|
| 7,320,984 B2* | 1/2008 | Izumimoto et al. | 514/282 |
| 2006/0040970 A1* | 2/2006 | Izumimoto et al. | 514/289 |

FOREIGN PATENT DOCUMENTS

| | | |
|---|---|---|
| JP | 41-18824 | 9/1941 |
| JP | 41-18826 | 9/1941 |
| JP | 11-501627 | 2/1999 |
| JP | 2004-522706 | 7/2004 |
| WO | WO 95/03308 A1 | 2/1995 |
| WO | WO 96/27375 A2 | 9/1996 |
| WO | WO 01/05795 A1 | 1/2001 |
| WO | WO 02/36573 A2 | 5/2002 |
| WO | WO 2004/033457 A1 | 4/2004 |
| WO | WO 2005/094826 A1 | 10/2005 |

OTHER PUBLICATIONS

L.M. Sayre et al., "Design and Synthesis of Naltrexone-Derived Affinity Labels with Nonequilibrium Opioid Agonist and Antagonist Activities. Evidence for the Existence of Different μ Receptor Subtypes in Different Tissues," J. Med. Chem., 1984, vol. 27, No. 10, pp. 1325-1335.

Csaba Simon et al., "Application of the Mitsunobu Reaction for Morphine Compounds. Preparation of 6β-Aminomorphine and Codeine Derivatives," Synthetic Communications, 1992, vol. 2, No. 6, pp. 913-921.

Csaba Simon et al., "Stereoselective Synthesis of β-Naltrexol, β-Naloxol, β-Naloxamine, β-Naltrexamine and Related Compounds by the Application of the Mitsunobu Reaction," Tetrahedron, 1994, vol. 50, No. 32, pp. 9757-9768.

S.R. Chaplan et al., "Quantitative Assessment of Tactile Allodynia in the Rat Paw," Journal of Neuroscience Methods, 1994, vol. 53, pp. 55-63.

Small, L et al., "The Aminomorphides and Aminocodides," Journal of the American Chemical Society, 1939, vol. 61, pp. 2186-2190.

Klinder, T. et al., "Syntheses of Novel Pyridazinomorphinans by Inverse Electron Demand Cycloaddition and their Binding to μ and κ Receptors," Arch. Pharm. Pharm. Med. Chem., 1997, vol. 330, pp. 163-168.

* cited by examiner

ANALGESIC AND METHODS OF TREATING PAIN

RELATED APPLICATION

This is a §371 of International Application No. PCT/JP2005/020297, with an international filing date of Nov. 4, 2005 (WO 2006/049248 A1, published May 11, 2006), which is based on Japanese Patent Application No. 2004-320583, filed Nov. 4, 2004.

TECHNICAL FIELD

This disclosure relates to an analgesic useful for treating pain, which comprises as an effective ingredient a morphinan derivative having a nitrogen-containing heterocyclic group, or a pharmaceutically acceptable acid addition salt thereof.

BACKGROUND ART

Causes of pain are known to include the cases where a tissue is damaged by a disease or injury so that an algesic substance is topically produced, and the cases wherein there is no direct factor such as noxious stimulus, but the pain is caused by dysfunction of nerve system or the like. Pain may be largely classified into 3 groups depending on the cause, that is, (1) nociceptive pain, (2) neuropathic pain and (3) psychogenic pain. The "nociceptive pain" is the pain caused by an external stimulus such as injury and the pain caused by a lesion in an internal tissue. Most of this type of pain is transient, which disappears when the underlying disease is cured, so that it is usually classified into acute pain. On the other hand, chronic pain is caused by dysfunction of central nervous system due to abnormality of a peripheral tissue or terminal portion of peripheral nerve, or due to damage of peripheral nerve, or caused by damage of central nervous system or psychologic mechanism. The above-mentioned neuropathic pain and the psychogenic pain belong to this chronic pain. Although pain is caused by various factors and its expression mechanism has not been well understood, reported endogenous substances related to pain and its regulation include bradykinin, histamine, prostaglandin, serotonin, substance P and opioid peptides.

As the therapeutic drugs against mild pain, nonsteroidal anti-inflammatory drugs (NSAIDs) such as aspirin and acetaminophen, having a site of action in the periphery have been used. As the therapeutic drugs against moderate or severe pain, opioid analgesics typified by morphine, having a site of action in the central nervous system have been used. However, the peripheral analgesics such as NSAIDs have a problem in that they have a side effect against digestive, in addition to the fact that the analgesic effects thereof are not sufficient in some cases. The opioid analgesics have a problem in that they have side effects such as nausea, vomiting, constipation and dependence. Further, although the analgesics typified by morphine exhibit effects against acute pain, they do not exhibit sufficient effects against neuropathic pain and psychogenic pain in most cases. Thus, creation of a novel analgesic which is not only effective against acute pain, but also effective against the chronic pain for which morphine is not effective, of which side effect is small, is demanded.

It is known for a long time that morphinan compounds typified by morphine have analgesic effects. Even limiting the morphinan compounds to those having a nitrogen-containing cyclic group on the 6-position, it has already been suggested that cyclic secondary amino compounds have analgesic effect (see Japanese Patent Publication (Kokoku) S41-18824, Japanese Patent Publication (Kokoku) S41-18826 and International Patent Publication No. WO 95/03308). Further, chemical structures of some of the morphinan compounds having a cyclic imide group on the 6-position have been disclosed, although the analgesic activities thereof have not been directly disclosed (see Csaba Simon et al., Tetrahedron, 1994, Vol. 50, No. 32, pp. 9757-9768, L. M. Sayre et al., Journal of Medicinal Chemistry, 1984, Vol. 27, No. 10, pp. 1325-1335 and Csaba Simon et al., Synthetic Communications, 1992, Vol. 2, No. 6, pp. 913-921). On the other hand, separately from these, it has been disclosed that the compounds have therapeutic effects against frequent urination and urinary incontinence (see International Patent Publication No. WO 2004/033457 (European Patent Publication No. EP 1 555 266 A1). Their antipruritic activities have also been disclosed, although the date of disclosure is after the priority date of the present application (International Patent Publication No. WO 2005/094826). However, none of these disclosed information infer that the compounds may be used as valuable analgesics which have potent analgesic effects and which may also be applied to chronic pain.

SUMMARY

We intensively studied among the morphinan compounds having a nitrogen-containing cyclic substituent on the 6-position and found that certain compounds having an acylamino substructure have drastically higher analgesic effect than the compounds having a cyclic amino group. Further, we discovered that the compounds are useful for therapies against various pain ranging from acute pain to chronic pain.

That is, we provide an analgesic comprising as an effective ingredient a morphinan derivative having a nitrogen-containing heterocyclic group, represented by the Formula (I):

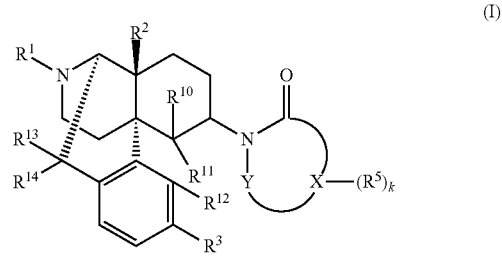

[wherein $R^1$ is hydrogen, $C_1$-$C_5$ alkyl, $C_4$-$C_7$ cycloalkylalkyl, $C_5$-$C_8$ cycloalkenylalkyl, $C_6$-$C_{12}$ aryl, $C_7$-$C_{13}$ aralkyl, $C_3$-$C_7$ alkenyl, furanylalkyl (wherein the number of carbon atoms in the alkyl moiety is 1 to 5), thienylalkyl (wherein the number of carbon atoms in the alkyl moiety is 1 to 5) or pyridylalkyl (wherein the number of carbon atoms in the alkyl moiety is 1 to 5);

$R^2$ and $R^3$ are independently hydrogen, hydroxy, $C_1$-$C_5$ alkoxy, $C_3$-$C_7$ alkenyloxy, $C_7$-$C_{13}$ aralkyloxy or $C_1$-$C_5$ alkanoyloxy;

—X— is $C_2$-$C_7$ alkylene, $C_2$-$C_7$ alkenylene or $C_2$-$C_7$ alkynylene, (one or more carbon atoms therein may be replaced by nitrogen, oxygen and/or sulfur atom) constituting a part of the ring structure;

Y represents valence bond, —C(=O)—, —C(=S)—, —S(O)—, —S(O$_2$)—, —N(—R$^4$)—, —C(=O)—N(—R$^4$)— or —C(=S)—N(—R$^4$)—;

$R^4$ is hydrogen or $C_1$-$C_5$ alkyl;

k is an integer of 0 to 8;

$R^5$ is (are) (a) substituent(s) in the number of k on a cyclic structure, which independently is (are) fluoro, chloro, bromo, iodo, nitro, $C_1$-$C_5$ alkyl, $C_1$-$C_5$ alkylidene, $C_7$-$C_{13}$ cycloalkylalkyl, $C_7$-$C_{13}$ cycloalkylalkylidene, $C_6$-$C_{12}$ aryl, $C_7$-$C_{13}$ aralkyl, $C_7$-$C_{13}$ aralkylidene, $C_6$-$C_{12}$ aryloxy, trifluoromethyl, trifluoromethoxy, cyano, isothiocyanato, $(CH_2)_pSR^7$, $(CH_2)_pS(O)R^7$, $(CH_2)_pS(O_2)R^7$, $(CH_2)_pOR^7$, $(CH_2)_pC(=O)R^7$, $(CH_2)_pOC(=O)R^7$, $(CH_2)_pCO_2R^7$, $(CH_2)_pS(O)NR^8R^9$, $(CH_2)_pS(O_2)NR^8R^9$, $(CH_2)_pC(=O)NR^8R^9$, $(CH_2)_pNR^8R^9$, $(CH_2)_pN(R^8)C(=O)R^9$ or $(CH_2)_pN(R^8)S(O_2)R^9$, or among the $R^5$s in the number of k, two $R^5$s bound to the same carbon atom or to the same sulfur atom cooperatively represent one oxygen atom to form carbonyl or sulfoxide, or two $R^5$s bound to the same carbon atom cooperatively represent one sulfur atom to form thiocarbonyl, or four $R^5$s bound to the same sulfur atom cooperatively represent two oxygen atoms to form sulfone, or among the $R^5$s in the number of k, two $R^5$s bound to adjacent carbon atoms, respectively, cooperatively form benzo, pyrido, naphtho, cyclopropano, cyclobutano, cyclopentano, cyclopenteno, cyclohexano, cyclohexeno, cycloheptano or cycloheptano, each of these rings formed with said two $R^5$s bound to adjacent carbon atoms being non-substituted or substituted with 1 or more $R^6$s;

$R^6$(s) independently is (are) fluoro, chloro, bromo, iodo, nitro, $C_1$-$C_5$ alkyl, $C_7$-$C_{13}$ aralkyl, trifluoromethyl, trifluoromethoxy, cyano, $C_6$-$C_{12}$ aryl, isothiocyanato, $(CH_2)_pSR^7$, $(CH_2)_pS(O)R^7$, $(CH_2)_pS(O_2)R^7$, $(CH_2)_pOR^7$, $(CH_2)_pC(=O)R^7$, $(CH_2)_pOC(=O)R^7$, $(CH_2)_pCO_2R^7$, $(CH_2)_pS(O)NR^8R^9$, $(CH_2)_pS(O_2)NR^8R^9$, $(CH_2)_pC(=O)NR^8R^9$, $(CH_2)_pNR^8R^9$, $(CH_2)_pN(R^8)C(=O)R^9$ or $(CH_2)_pN(R^8)S(O_2)R^9$;

p is an integer of 0 to 5;

$R^7$, $R^8$ and $R^9$ are independently hydrogen, $C_1$-$C_5$ alkyl, $C_3$-$C_7$ alkenyl, $C_6$-$C_{12}$ aryl, or $C_7$-$C_{13}$ aralkyl;

$R^{10}$ is hydrogen, $C_1$-$C_5$ alkyl, $C_2$-$C_5$ alkenyl, $C_7$-$C_{13}$ aralkyl, $(CH_2)_pOR^7$ or $(CH_2)_pCO_2R^7$ (wherein p and $R^7$ represent the same meanings as described above);

$R^{11}$ and $R^{12}$ are bound to form —O—, —S— or —$CH_2$—, or $R^{11}$ is hydrogen and $R^{12}$ is hydrogen, hydroxy, $C_1$-$C_5$ alkoxy or $C_1$-$C_5$ alkanoyloxy;

$R^{13}$ and $R^{14}$ cooperatively represent oxo, or $R^{13}$ is hydrogen and $R^{14}$ is hydrogen, hydroxy, $C_1$-$C_5$ alkoxy or $C_1$-$C_5$ alkanoyloxy;

and the Formula (I) includes (+), (−) and (±) isomers]
or a pharmaceutically acceptable acid addition salt thereof.

The pain which is treated by the analgesic includes neuropathic pain, diabetic neuralgia and chronic pelvic visceral pain. We further provide a method for relieving or allaying pain, comprising administering an effective amount of one or more of the above-described morphinan derivatives having a nitrogen-containing heterocyclic group and the pharmaceutically acceptable acid addition salt thereof. We still further provide a use of the above-described morphinan derivative having a nitrogen-containing heterocyclic group, or the pharmaceutically acceptable acid addition salt thereof, for the production of an analgesic.

The morphinan derivatives having a nitrogen-containing heterocyclic group have highly potent analgesic effects and may be used as excellent analgesics effective for therapies of various pain ranging from acute pain to chronic pain.

DETAILED DESCRIPTION

Figure 1:
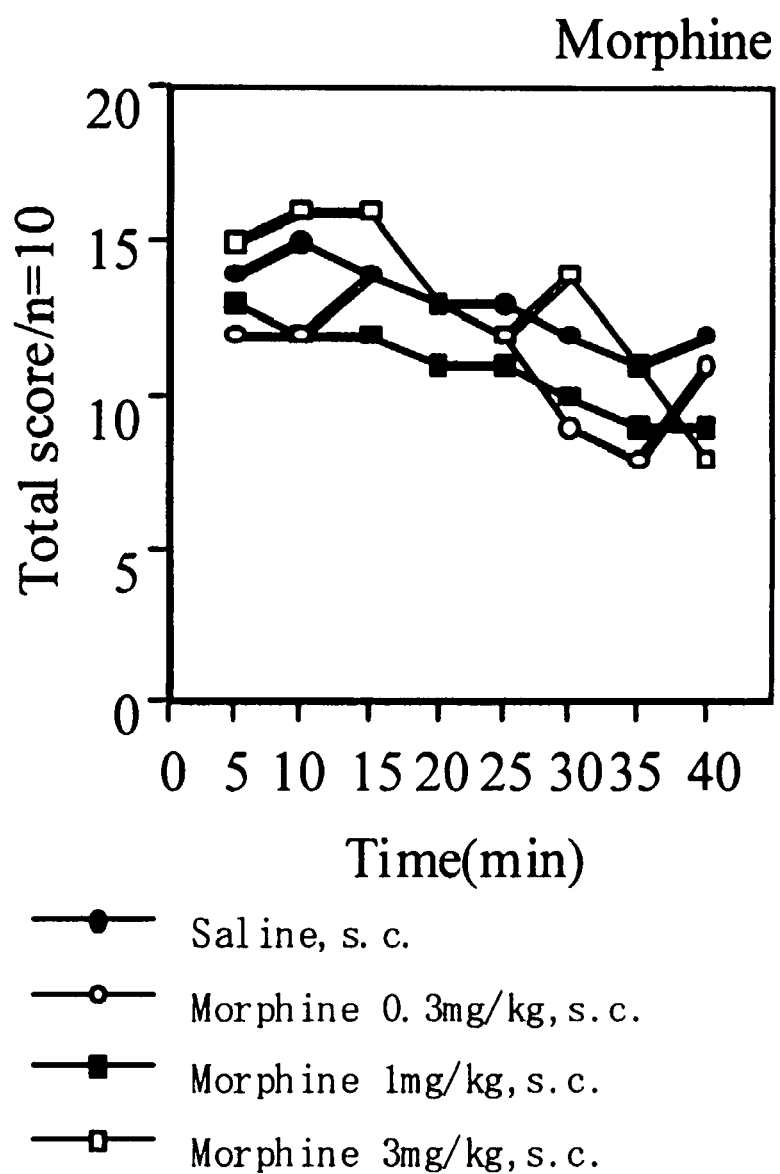
FIG. 1. shows the results of the experiment, as a comparative example, using Morphine in the $PGF_2\alpha$-induced allodynia model method.
Figure 2:
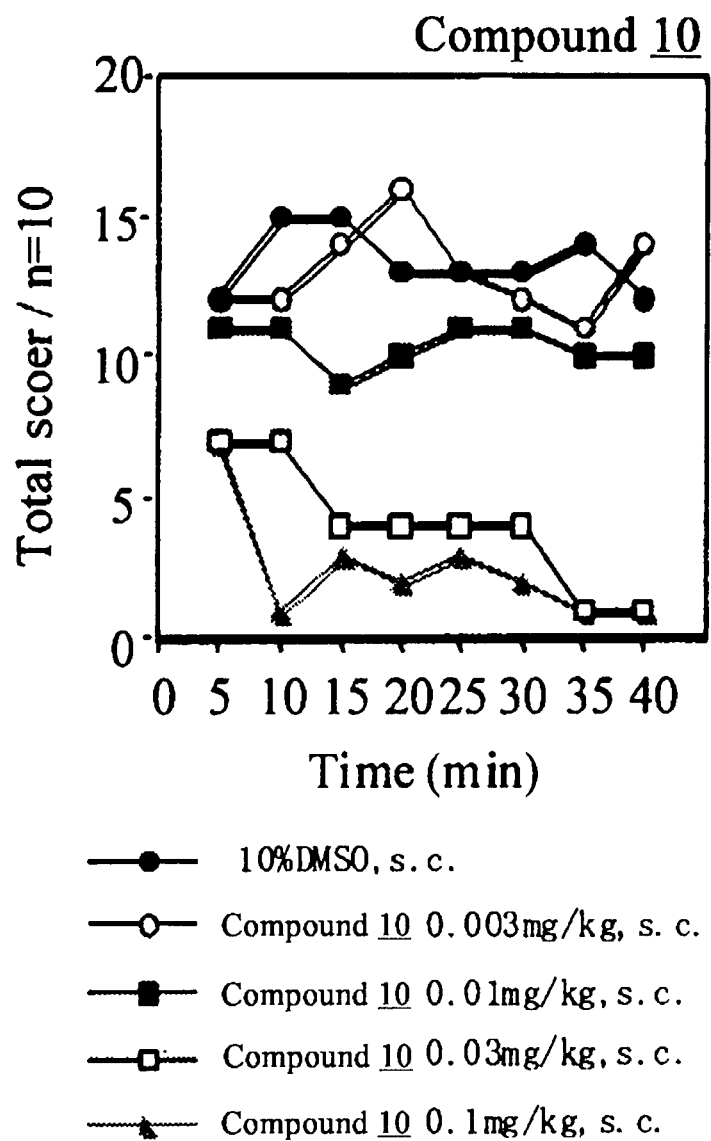
FIG. 2. shows the results of the experiment for confirming the analgesic activity of Compound 10, by the $PGF_2\alpha$-induced allodynia model method.
Figure 3:
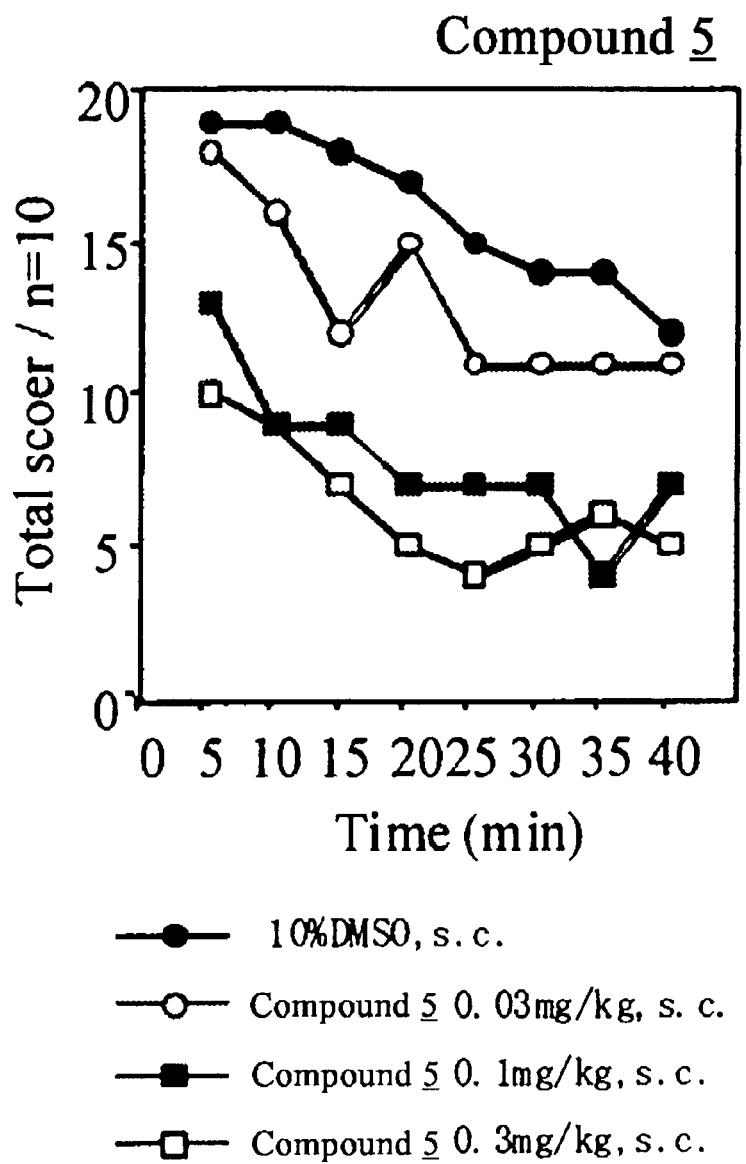
FIG. 3. shows the results of the experiment for confirming the analgesic activity of Compound 5, by the $PGF_2\alpha$-induced allodynia model method.
Figure 4:
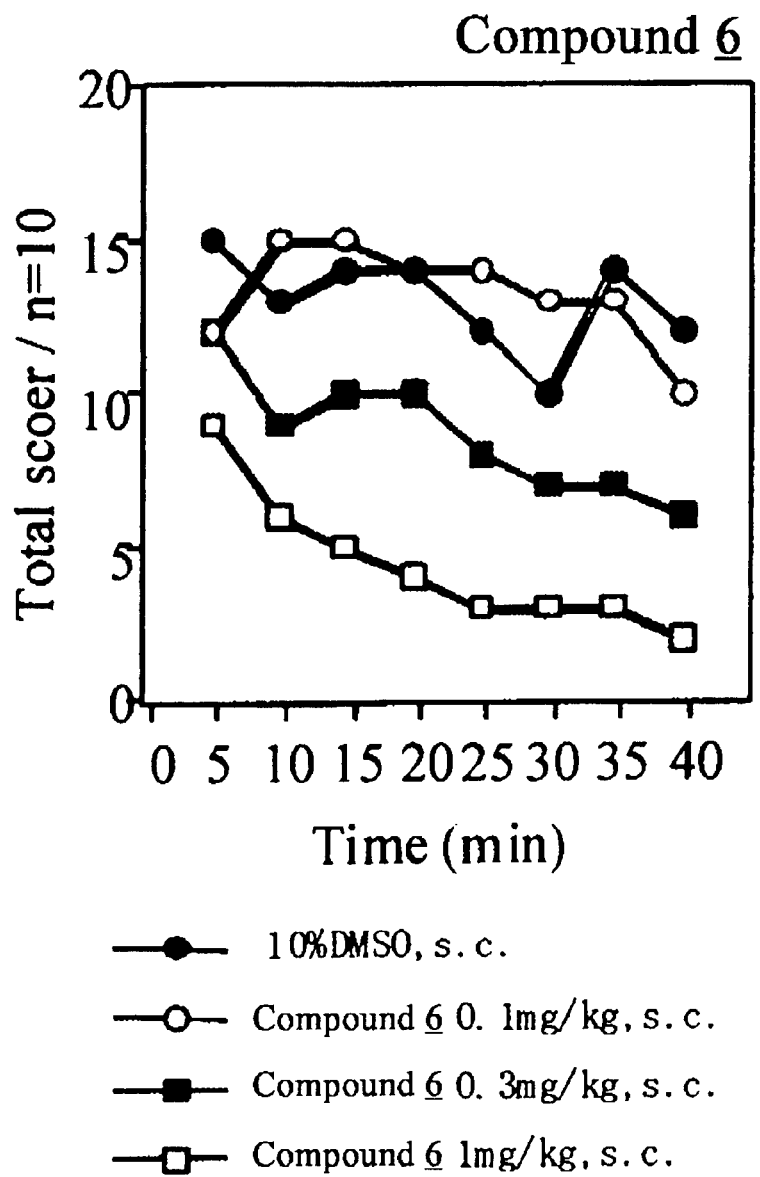
FIG. 4. shows the results of the experiment for confirming the analgesic activity of Compound 6, by the $PGF_2\alpha$-induced allodynia model method.

As mentioned above, the analgesic comprises as an effective ingredient a morphinan derivative having a nitrogen-containing heterocyclic group, represented by Formula (I) or a pharmaceutically acceptable acid addition salt thereof.

In Formula (I), $R^1$ is preferably hydrogen, $C_4$-$C_7$ cycloalkylalkyl, $C_5$-$C_8$ cycloalkenylalkyl, $C_6$-$C_{12}$ aryl or $C_3$-$C_7$ alkenyl. Among these, more preferred are hydrogen, cyclopropylmethyl, 2-cyclopropylethyl, 3-cyclopropylpropyl, 4-cyclopropylbutyl, cyclobutyl-methyl, cyclopentylmethyl, cyclohexylmethyl, cyclobutenylmethyl, 2-cyclobutenylethyl, 3-cyclobutenylpropyl, phenyl, naphthyl, tolyl, allyl and prenyl. Among these, more preferred are hydrogen, cyclopropylmethyl, cyclobutylmethyl, cyclopentylmethyl, cyclohexylmethyl, allyl and prenyl, and especially preferred are hydrogen, cyclopropylmethyl, cyclobutylmethyl and allyl.

$R^2$ and $R^3$ are independently and preferably hydrogen, hydroxy, methoxy, ethoxy, allyloxy, benzyloxy, acetoxy or propionoxy. Among these, hydrogen, hydroxy, methoxy and acetoxy are preferred.

—X— is preferably $C_2$-$C_4$ alkylene or $C_2$-$C_4$ alkenylene constituting a part of the cyclic structure, more preferably, ethylene (—$CH_2$—$CH_2$—), vinylene (—CH=CH—), propylene (—$CH_2$—$CH_2$—$CH_2$—) or propenylene (—$CH_2$—CH=CH—). Y is preferably valence bond or —(C=O)—, and especially preferably —(C=O)—.

k is an integer of 0 to 6, and preferably 1 or 2, especially preferably 2.

When k is 1, $R^5$ is preferably $C_1$-$C_5$ alkyl, $C_1$-$C_5$ alkylidene, $C_7$-$C_{13}$ cycloalkylalkyl, $C_6$-$C_{12}$ aryl, $C_7$-$C_{13}$ aralkyl, $C_7$-$C_{13}$ aralkylidene, $C_7$-$C_{13}$ cycloalkylalkylidene or $C_6$-$C_{12}$ aryloxy, more preferably methyl, ethyl, ethylidene, propyl, propylidene, butyl, butylidene, benzyl, benzylidene, methylbenzyl, methylbenzylidene, fluorobenzyl, fluorobenzylidene, trifluoromethoxybenzyl, trifluoromethoxybenzylidene, phenethyl, phenethylidene, cyclohexylmethyl, cyclohexylmethylidene, phenoxy or chlorophenoxy. When k is 2, it is preferred that two $R^5$s bound to adjacent carbon atoms, respectively, cooperatively form benzo, pyrido, naphtho, cyclopropano, cyclobutano, cyclopentano, cyclopenteno, cyclohexano, cyclohexeno, cycloheptano or cyclohepteno, more preferably benzo or cyclohexeno, especially preferably benzo, each of these rings mentioned above formed with the two $R^5$s is non-substituted or substituted with 1 or more $R^6$s.

Although the benzo or cyclohexeno may preferably be non-substituted, the substituent(s) $R^6$(s) is (are) also preferably and independently fluoro, chloro, bromo, iodo, nitro, $C_1$-$C_5$ alkyl (especially, methyl, ethyl or propyl), $C_7$-$C_{13}$ aralkyl (especially benzyl), methoxy, ethoxy, trifluoromethyl, trifluoromethoxy, cyano, $C_6$-$C_{12}$ aryl (especially phenyl), isothiocyanato, $SR^7$, $S(O)R^7$, $S(O_2)R^7$, $(CH_2)_pOR^7$, $(CH_2)_pC(=O)R^7$, $(CH_2)_pCO_2R^7$, $S(O)NR^8R^9$, $S(O_2)NR^8R^9$, $C(=O)NR^8R^9$, $(CH_2)_pNR^8R^9$ or $(CH_2)_pN(R^8)C(=O)R^9$ (wherein p is an integer of 0 to 5, $R^7$ is hydrogen, $C_1$-$C_5$ alkyl (especially methyl, ethyl or propyl), $C_3$-$C_7$ alkenyl or $C_6$-$C_{12}$ aryl (especially phenyl), $R^8$ and $R^9$ are preferably and independently hydrogen, $C_1$-$C_5$ alkyl (especially methyl, ethyl or propyl), or $C_7$-$C_{13}$ aralkyl (especially benzyl)). In addition to the cases where the benzo or cyclohexeno is not substituted, $R^6$(s) is (are) more preferably and independently, fluoro, chloro, bromo, iodo, nitro, methyl, ethyl, propyl, benzyl, hydroxy, methoxy, ethoxy, trifluoromethyl, trifluoromethoxy, cyano, phenyl, hydroxymethyl, hydroxyethyl, isothiocyanato, mercapto, methylthio, methylsulfinyl, methylsulfonyl, methoxymethyl, ethoxymethyl, methoxyethyl, acetoxy, phenoxy, methoxycarbonyl, ethoxycarbonyl, methoxycarbonylmethyl, ethoxycarbonylmethyl, sulfamoyl, dimethylsulfamoyl, dimethylcarbamoyl, dimethylamino, dimethylaminomethyl, dimethylaminoethyl, amino, acetamino or acetaminomethyl.

$R^{10}$ is preferably hydrogen, $C_1$-$C_5$ alkyl, allyl or benzyl, more preferably hydrogen or methyl.

$R^{11}$ and $R^{12}$ are preferably bound to form —O—, or preferably, $R^{11}$ is hydrogen and $R^{12}$ is hydrogen, hydroxy or methoxy, and more preferably, $R^{11}$ and $R^{12}$ are bound to form —O—.

$R^{13}$ and $R^{14}$ preferably cooperatively represent oxo, or preferably, $R^{13}$ is hydrogen and $R^{14}$ is hydrogen or hydroxy, and more preferably, both $R^{13}$ and $R^{14}$ are hydrogen, that is, the one which is not substituted is more preferred.

Preferred examples of the pharmaceutically acceptable acid addition salts include inorganic acid salts such as hydrochloric acid salt, sulfuric acid salt, nitric acid salt, hydrobromic acid salt, hydroiodic acid salt and phosphoric acid salt; organic carboxylic acid salts such as acetic acid salt, lactic acid salt, citric acid salt, oxalic acid salt, glutaric acid salt, malic acid salt, tartaric acid salt, fumaric acid salt, mandelic acid salt, maleic acid salt, benzoic acid salt and phthalic acid salt; and organic sulfonic acid salts such as methanesulfonic acid salt, ethanesulfonic acid salt, benzenesulfonic acid salt, p-toluenesulfonic acid salt and camphorsulfonic acid salt. Among these, hydrochloric acid salt, tartaric acid salt, methanesulfonic acid salt, maleic acid salt and the like are preferred, but the acid addition salt is not restricted thereto.

The compounds having the above-described preferred substituents in combination as well as their acid addition salts are preferred.

The compounds having the following substituents as the substituents in Formula (I) are also preferred. That is, (1) Those wherein in Formula (I), —X— is $C_2$-$C_7$ alkylene, $C_2$-$C_7$ alkenylene or $C_2$-$C_7$ alkynylene; $R^5$ is (are) (a) substituent(s) in the number of k on the —X—, which independently is (are) fluoro, chloro, bromo, iodo, nitro, $C_1$-$C_5$ alkyl, $C_1$-$C_5$ alkylidene, $C_7$-$C_{13}$ cycloalkylalkyl, $C_7$-$C_{13}$ cycloalkylalkylidene, $C_6$-$C_{12}$ aryl, $C_7$-$C_{13}$ aralkyl, $C_7$-$C_{13}$ aralkylidene, trifluoromethyl, trifluoromethoxy, cyano, isothiocyanato, $(CH_2)_pOR^7$, $(CH_2)_pC(=O)R^7$, $(CH_2)_pCO_2R^7$, $(CH_2)_pNR^8R^9$ or $(CH_2)_pN(R^8)C(=O)R^9$, or among the $R^5$s in the number of k, two $R^5$s bound to adjacent carbon atoms, respectively, cooperatively form benzo, pyrido, naphtho, cyclopropano, cyclobutano, cyclopentano, cyclopenteno, cyclohexano, cyclohexeno, cycloheptano or cyclohepteno, each of these rings formed with said two $R^5$s bound to adjacent carbon atoms being non-substituted or substituted with 1 or more $R^6$s;

$R^6$(s) independently is (are) fluoro, chloro, bromo, iodo, nitro, $C_1$-$C_5$ alkyl, trifluoromethyl, trifluoromethoxy, cyano, $C_6$-$C_{12}$ aryl, isothiocyanato, $(CH_2)_pOR^7$, $(CH_2)_pC(=O)R^7$, $(CH_2)_pCO_2R^7$, $(CH_2)_pNR^8R^9$ or $(CH_2)_pN(R^8)C(=O)R^9$;

$R^8$ and $R^9$ are independently hydrogen, $C_1$-$C_5$ alkyl or $C_7$-$C_{13}$ aralkyl; and both $R^{13}$ and $R^{14}$ are hydrogen and acid addition salts thereof;

(2) Those compounds of (1) wherein —X— is $C_2$ alkylene or alkenylene and acid addition salts thereof;

(3) Those wherein in Formula (I), —X— is $C_2$-$C_4$ alkylene or alkenylene constituting a part of the ring structure; Y represents valence bond or —C(=O)—; k is 1 or 2; $R^5$ is (are) $C_1$-$C_5$ alkyl, $C_1$-$C_5$ alkylidene, $C_7$-$C_{13}$ cycloalkylalkyl, $C_7$-$C_{13}$ cycloalkylalkylidene, $C_6$-$C_{12}$ aryl, $C_7$-$C_{13}$ aralkyl, $C_7$-$C_{13}$ aralkylidene, or two $R^5$s bound to adjacent carbon atoms, respectively, cooperatively form benzo, pyrido, naphtho, cyclopropano, cyclobutano, cyclopentano, cyclopenteno, cyclohexano, cyclohexeno, cycloheptano or cyclohepteno, each of these rings formed with said two $R^5$s bound to adjacent carbon atoms being non-substituted or substituted with 1 or more $R^6$s; $R^7$ is hydrogen, methyl, ethyl, propyl or phenyl; $R^8$ and $R^9$ independently are hydrogen, methyl, ethyl, propyl or benzyl; and $R^{10}$ is hydrogen, $C_1$-$C_5$ alkyl, allyl or benzyl and acid addition salts thereof;

(4) Those compounds of (3) wherein $R^1$ hydrogen, $C_4$-$C_7$ cycloalkylalkyl, $C_5$-$C_8$ cycloalkenylalkyl, $C_6$-$C_{12}$ aryl or $C_3$-$C_7$ alkenyl; $R^5$ is methyl, ethyl, ethylidene, propyl, propylidene, butyl, butylidene, benzyl, benzylidene, methylbenzyl, methylbenzylidene, fluorobenzyl, fluorobenzylidene, trifluoromethoxybenzyl, trifluoromethoxybenzylidene, phenethyl, phenethylidene, cyclohexylmethyl, cyclohexylmethylidene, phenoxy or chlorophenoxy, or two $R^5$s bound to adjacent carbon atoms, respectively, cooperatively form benzo, pyrido, naphtho, cyclopropano, cyclobutano, cyclopentano, cyclopenteno, cyclohexano, cyclohexeno, cycloheptano or cyclohepteno, each of these rings formed with said two $R^5$s bound to adjacent carbon atoms being non-substituted or substituted with 1 or more $R^6$s; and $R^{11}$ and $R^{12}$ are bound to form —O—, or $R^{11}$ is hydrogen and $R^{12}$ is hydrogen, hydroxy or methoxy and acid addition salts thereof;

(5) Those compounds of (4) wherein $R^1$ is hydrogen, cyclopropylmethyl, 2-cyclopropylethyl, 3-cyclopropylpropyl, 4-cyclopropylbutyl, cyclobutylmethyl, cyclopentylmethyl, cyclohexylmethyl, cyclobutenylmethyl, 2-cyclobutenylethyl, 3-cyclobutenylpropyl, phenyl, naphthyl, tolyl, allyl or prenyl; k is 2; and two $R^5$s bound to adjacent carbon atoms, respectively, cooperatively form benzo, pyrido, naphtho, cyclopropano, cyclobutano, cyclopentano, cyclopenteno, cyclohexano, cyclohexeno, cyclo-heptano or cyclohepteno, each of these rings formed with said two $R^5$s bound to adjacent carbon atoms being non-substituted or substituted with 1 or more R⁶s and acid addition salts thereof;

(6) Those compounds of (5) wherein $R^1$ is hydrogen, cyclopropylmethyl, cyclobutylmethyl, allyl or prenyl; $R^2$ and $R^3$ independently are hydrogen, hydroxy, methoxy, ethoxy, allyloxy, benzyloxy, acetoxy or propionoxy; —X— is ethylene, vinylene, propylene or propenylene; two $R^5$s bound to adjacent carbon atoms, respectively, cooperatively form benzo or cyclohexeno, each of these rings formed with said two $R^5$s bound to adjacent carbon atoms being non-substituted or substituted with 1 to 4 $R^6$s; $R^{10}$ is hydrogen or methyl; and $R^{11}$ and $R^{12}$ are bound to form —O— and acid addition salts thereof; and (7) Those compounds of (6) wherein in Formula (I), $R^1$ is hydrogen, cyclopropylmethyl, cyclobutylmethyl or allyl; $R^2$ and $R^3$ independently are hydrogen, hydroxy, methoxy or acetoxy; —X— is vinylene; Y is —C(=O)—; two $R^5$s bound to adjacent carbon atoms, respectively, cooperatively form benzo which is non-substituted or substituted with 1 to 4 $R^6$s; $R^6$(s) independently is (are) fluoro, chloro, bromo, iodo, nitro, methyl, ethyl, propyl, benzyl, hydroxy, methoxy, ethoxy, trifluoromethyl, trifluoromethoxy, cyano, phenyl, hydroxymethyl, hydroxyethyl, isothiocyanato, mercapto, methylthio, methylsulfinyl, methylsulfonyl, methoxymethyl, ethoxymethyl, methoxyethyl, acetoxy, phenoxy, methoxycarbonyl, ethoxycarbonyl, methoxycarbonylmethyl, ethoxycarbonylmethyl, sulfamoyl, dimethylsulfamoyl, dimethylcarbamoyl, dimethylamino, dimethylaminomethyl, dimethylaminoethyl, amino, acetamino, acetaminomethyl or methanesulfonamide; $R^{10}$ is hydrogen; and both $R^{13}$ and $R^{14}$ are hydrogen and acid addition salts thereof.

Among the compounds represented by Formula (I), specific examples of the compounds wherein —X— is vinylene, Y is —C(=O)—, k is 2, two $R^5$s bound to adjacent carbon atoms, respectively, cooperatively form benzo which is non-substituted or substituted with $R^{6a}$, $R^{6b}$, $R^{6c}$ or $R^{6d}$ ($R^{6a}$, $R^{6b}$, $R^{6c}$ and $R^{6d}$ have the same meanings as the above-described $R^6$) or an arbitrary combination thereof, $R^{10}$, $R^{13}$ and $R^{14}$ are hydrogen, $R^{11}$ and $R^{12}$ are bound to form —O—, that is, the compounds represented by the Formula (Ia) below are shown in Table 1. In the tables described below, CPM means cyclopropylmethyl, "–" means that the substituent is not shown in the formula, and the bond at 6-position is α or β.

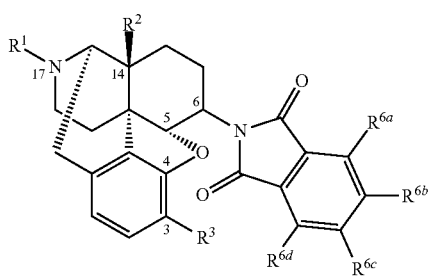

(Ia)

Among the compounds represented by Formula (Ia), the compound wherein $R^1$ is cyclopropylmethyl, $R^2$ and $R^3$ are hydroxy, $R^{6b}$ is fluorine, and the configuration of the bond at the 6-position is β, that is, the compound of the following formula:

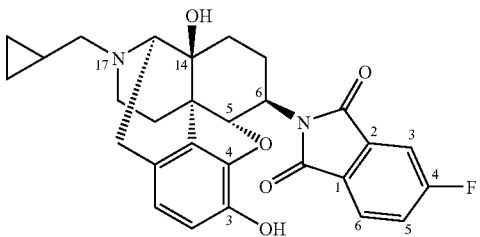 [SMILES: O=C1c2ccc(F)cc2C(=O)N1[C@@H]1CC[C@@]2(O)[C@H]3Cc4ccc(O)c5c4[C@@]2(CCN3CC2CC2)[C@H]1O5]

is named N-[17-(cyclopropylmethyl)-4,5α-epoxy-3,14-dihydroxymorphinan-6β-yl]-4-fluorophthalimide.

TABLE 1

| $R^1$ | $R^2$ | $R^3$ | $R^{6a}$ | $R^{6b}$ | $R^{6c}$ | $R^{6d}$ |
|---|---|---|---|---|---|---|
| CPM | OH | OH | — | — | — | — |
| CPM | OH | OH | F | — | — | — |
| CPM | OH | OH | — | F | — | — |
| CPM | OH | OH | F | — | — | F |
| CPM | OH | OH | — | F | F | — |
| CPM | OH | OH | F | F | F | F |
| CPM | OH | OH | Cl | — | — | — |
| CPM | OH | OH | — | Cl | — | — |
| CPM | OH | OH | Cl | — | — | Cl |
| CPM | OH | OH | — | Cl | Cl | — |
| CPM | OH | OH | Br | — | — | — |
| CPM | OH | OH | — | Br | — | — |
| CPM | OH | OH | Br | — | — | Br |
| CPM | OH | OH | — | Br | Br | — |
| CPM | OH | OH | Me | — | — | — |
| CPM | OH | OH | — | Me | — | — |
| CPM | OH | OH | Me | — | — | Me |
| CPM | OH | OH | — | Me | Me | — |
| CPM | OH | OH | OMe | — | — | — |
| CPM | OH | OH | — | OMe | — | — |
| CPM | OH | OH | OMe | — | — | OMe |
| CPM | OH | OH | — | OMe | OMe | — |
| CPM | OH | OH | OH | — | — | — |
| CPM | OH | OH | — | OH | — | — |
| CPM | OH | OH | OH | — | — | OH |
| CPM | OH | OH | — | OH | OH | — |
| CPM | OH | OH | $NO_2$ | — | — | — |
| CPM | OH | OH | — | $NO_2$ | — | — |
| CPM | OH | OH | $NO_2$ | — | — | $NO_2$ |
| CPM | OH | OH | — | $NO_2$ | $NO_2$ | — |
| CPM | OH | OH | $NH_2$ | — | — | — |
| CPM | OH | OH | — | $NH_2$ | — | — |
| CPM | OH | OH | $NH_2$ | — | — | $NH_2$ |
| CPM | OH | OH | — | $NH_2$ | $NH_2$ | — |
| Allyl | OH | OH | — | — | — | — |
| Allyl | OH | OH | F | — | — | — |
| Allyl | OH | OH | — | F | — | — |
| Allyl | OH | OH | F | — | — | F |
| Allyl | OH | OH | — | F | F | — |
| Allyl | OH | OH | F | F | F | F |
| Allyl | OH | OH | Cl | — | — | — |
| Allyl | OH | OH | — | Cl | — | — |
| Allyl | OH | OH | Cl | — | — | Cl |
| Allyl | OH | OH | — | Cl | Cl | — |
| Allyl | OH | OH | Br | — | — | — |
| Allyl | OH | OH | — | Br | — | — |
| Allyl | OH | OH | Br | — | — | Br |
| Allyl | OH | OH | — | Br | Br | — |
| Allyl | OH | OH | Me | — | — | — |
| Allyl | OH | OH | — | Me | — | — |
| Allyl | OH | OH | Me | — | — | Me |
| Allyl | OH | OH | — | Me | Me | — |
| Allyl | OH | OH | OMe | — | — | — |
| Allyl | OH | OH | — | OMe | — | — |
| Allyl | OH | OH | OMe | — | — | OMe |
| Allyl | OH | OH | — | OMe | OMe | — |
| Allyl | OH | OH | OH | — | — | — |
| Allyl | OH | OH | — | OH | — | — |
| Allyl | OH | OH | OH | — | — | OH |
| Allyl | OH | OH | — | OH | OH | — |

TABLE 1-continued

| R¹ | R² | R³ | $R^{6a}$ | $R^{6b}$ | $R^{6c}$ | $R^{6d}$ |
|---|---|---|---|---|---|---|
| Allyl | OH | OH | NO₂ | — | — | — |
| Allyl | OH | OH | — | NO₂ | — | — |
| Allyl | OH | OH | NO₂ | — | — | NO₂ |
| Allyl | OH | OH | — | NO₂ | NO₂ | — |
| Allyl | OH | OH | NH₂ | — | — | — |
| Allyl | OH | OH | — | NH₂ | — | — |
| Allyl | OH | OH | NH₂ | — | — | NH₂ |
| Allyl | OH | OH | — | NH₂ | NH₂ | — |
| CPM | H | OH | — | — | — | — |
| CPM | H | OH | F | — | — | — |
| CPM | H | OH | — | F | — | — |
| CPM | H | OH | F | — | — | F |
| CPM | H | OH | — | F | F | — |
| CPM | H | OH | F | F | F | F |
| CPM | H | OH | Cl | — | — | — |
| CPM | H | OH | — | Cl | — | — |
| CPM | H | OH | Cl | — | — | Cl |
| CPM | H | OH | — | Cl | Cl | — |
| CPM | H | OH | Br | — | — | — |
| CPM | H | OH | — | Br | — | — |
| CPM | H | OH | Br | — | — | Br |
| CPM | H | OH | — | Br | Br | — |
| CPM | H | OH | Me | — | — | — |
| CPM | H | OH | — | Me | — | — |
| CPM | H | OH | Me | — | — | Me |
| CPM | H | OH | — | Me | Me | — |
| CPM | H | OH | OMe | — | — | — |
| CPM | H | OH | — | OMe | — | — |
| CPM | H | OH | OMe | — | — | OMe |
| CPM | H | OH | — | OMe | OMe | — |
| CPM | H | OH | OH | — | — | — |
| CPM | H | OH | — | OH | — | — |
| CPM | H | OH | OH | — | — | OH |
| CPM | H | OH | — | OH | OH | — |
| CPM | H | OH | NO₂ | — | — | — |
| CPM | H | OH | — | NO₂ | — | — |
| CPM | H | OH | NO₂ | — | — | NO₂ |
| CPM | H | OH | — | NO₂ | NO₂ | — |
| CPM | H | OH | NH₂ | — | — | — |
| CPM | H | OH | — | NH₂ | — | — |
| CPM | H | OH | NH₂ | — | — | NH₂ |
| CPM | H | OH | — | NH₂ | NH₂ | — |
| Allyl | H | OH | — | — | — | — |
| Allyl | H | OH | F | — | — | — |
| Allyl | H | OH | — | F | — | — |
| Allyl | H | OH | F | — | — | F |
| Allyl | H | OH | — | F | F | — |
| Allyl | H | OH | F | F | F | F |
| Allyl | H | OH | Cl | — | — | — |
| Allyl | H | OH | — | Cl | — | — |
| Allyl | H | OH | Cl | — | — | Cl |
| Allyl | H | OH | — | Cl | Cl | — |
| Allyl | H | OH | Br | — | — | — |
| Allyl | H | OH | — | Br | — | — |
| Allyl | H | OH | Br | — | — | Br |
| Allyl | H | OH | — | Br | Br | — |
| Allyl | H | OH | Me | — | — | — |
| Allyl | H | OH | — | Me | — | — |
| Allyl | H | OH | Me | — | — | Me |
| Allyl | H | OH | — | Me | Me | — |
| Allyl | H | OH | OMe | — | — | — |
| Allyl | H | OH | — | OMe | — | — |
| Allyl | H | OH | OMe | — | — | OMe |
| Allyl | H | OH | — | OMe | OMe | — |
| Allyl | H | OH | OH | — | — | — |
| Allyl | H | OH | — | OH | — | — |
| Allyl | H | OH | OH | — | — | OH |
| Allyl | H | OH | — | OH | OH | — |
| Allyl | H | OH | NO₂ | — | — | — |
| Allyl | H | OH | — | NO₂ | — | — |
| Allyl | H | OH | NO₂ | — | — | NO₂ |
| Allyl | H | OH | — | NO₂ | NO₂ | — |
| Allyl | H | OH | NH₂ | — | — | — |
| Allyl | H | OH | — | NH₂ | — | — |
| Allyl | H | OH | NH₂ | — | — | NH₂ |
| Allyl | H | OH | — | NH₂ | NH₂ | — |
| CPM | OAc | OH | — | — | — | — |
| CPM | OAc | OH | F | — | — | — |
| CPM | OAc | OH | — | F | — | — |
| CPM | OAc | OH | F | — | — | F |
| CPM | OAc | OH | — | F | F | — |
| CPM | OAc | OH | F | F | F | F |
| CPM | OAc | OH | Cl | — | — | — |
| CPM | OAc | OH | — | Cl | — | — |
| CPM | OAc | OH | Cl | — | — | Cl |
| CPM | OAc | OH | — | Cl | Cl | — |
| CPM | OAc | OH | Br | — | — | — |
| CPM | OAc | OH | — | Br | — | — |
| CPM | OAc | OH | Br | — | — | Br |
| CPM | OAc | OH | — | Br | Br | — |
| CPM | OAc | OH | Me | — | — | — |
| CPM | OAc | OH | — | Me | — | — |
| CPM | OAc | OH | Me | — | — | Me |
| CPM | OAc | OH | — | Me | Me | — |
| CPM | OAc | OH | OMe | — | — | — |
| CPM | OAc | OH | — | OMe | — | — |
| CPM | OAc | OH | OMe | — | — | OMe |
| CPM | OAc | OH | — | OMe | OMe | — |
| CPM | OAc | OH | OH | — | — | — |
| CPM | OAc | OH | — | OH | — | — |
| CPM | OAc | OH | OH | — | — | OH |
| CPM | OAc | OH | — | OH | OH | — |
| CPM | OAc | OH | NO₂ | — | — | — |
| CPM | OAc | OH | — | NO₂ | — | — |
| CPM | OAc | OH | NO₂ | — | — | NO₂ |
| CPM | OAc | OH | — | NO₂ | NO₂ | — |
| CPM | OAc | OH | NH₂ | — | — | — |
| CPM | OAc | OH | — | NH₂ | — | — |
| CPM | OAc | OH | NH₂ | — | — | NH₂ |
| CPM | OAc | OH | — | NH₂ | NH₂ | — |
| Allyl | OAc | OH | — | — | — | — |
| Allyl | OAc | OH | F | — | — | — |
| Allyl | OAc | OH | — | F | — | — |
| Allyl | OAc | OH | F | — | — | F |
| Allyl | OAc | OH | — | F | F | — |
| Allyl | OAc | OH | F | F | F | F |
| Allyl | OAc | OH | Cl | — | — | — |
| Allyl | OAc | OH | — | Cl | — | — |
| Allyl | OAc | OH | Cl | — | — | Cl |
| Allyl | OAc | OH | — | Cl | Cl | — |
| Allyl | OAc | OH | Br | — | — | — |
| Allyl | OAc | OH | — | Br | — | — |
| Allyl | OAc | OH | Br | — | — | Br |
| Allyl | OAc | OH | — | Br | Br | — |
| Allyl | OAc | OH | Me | — | — | — |
| Allyl | OAc | OH | — | Me | — | — |
| Allyl | OAc | OH | Me | — | — | Me |
| Allyl | OAc | OH | — | Me | Me | — |
| Allyl | OAc | OH | OMe | — | — | — |
| Allyl | OAc | OH | — | OMe | — | — |
| Allyl | OAc | OH | OMe | — | — | OMe |
| Allyl | OAc | OH | — | OMe | OMe | — |
| Allyl | OAc | OH | OH | — | — | — |
| Allyl | OAc | OH | — | OH | — | — |
| Allyl | OAc | OH | OH | — | — | OH |
| Allyl | OAc | OH | — | OH | OH | — |
| Allyl | OAc | OH | NO₂ | — | — | — |
| Allyl | OAc | OH | — | NO₂ | — | — |
| Allyl | OAc | OH | NO₂ | — | — | NO₂ |
| Allyl | OAc | OH | — | NO₂ | NO₂ | — |
| Allyl | OAc | OH | NH₂ | — | — | — |
| Allyl | OAc | OH | — | NH₂ | — | — |
| Allyl | OAc | OH | NH₂ | — | — | NH₂ |
| Allyl | OAc | OH | — | NH₂ | NH₂ | — |

Among the compounds represented by Formula (I), specific examples of the compounds wherein —X— is propenylene (—CH₂—CH=CH—), Y is valence bond, two R⁵s bound to adjacent carbon atoms, respectively, cooperatively form benzo which is non-substituted or substituted with $R^{6a}$, $R^{6b}$, $R^{6c}$ or $R^{6d}$ ($R^{6a}$, $R^{6b}$, $R^{6c}$ and $R^{6d}$ have the same meanings as the above-described R⁶) or an arbitrary combination thereof, R¹⁰, R¹³ and R¹⁴ are hydrogen, R¹¹ and R¹² are bound to form —O—, that is, the compounds represented by the Formula (Ib) below are shown in Table 2.

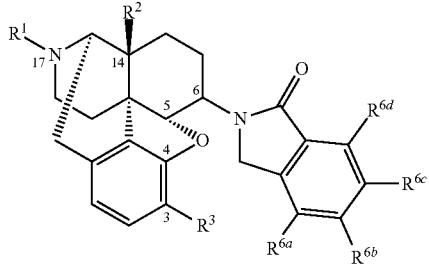

(Ib)

Among the compounds represented by Formula (Ib), the compound wherein $R^1$ is cyclopropylmethyl, $R^2$ and $R^3$ are hydroxy, $R^{6c}$ is fluorine, and the configuration of the bond at the 6-position is β, that is, the compound of the following formula:

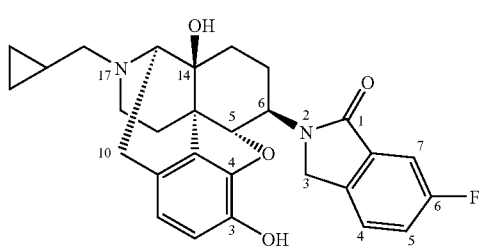 [SMILES: O=C1c2cc(F)ccc2CN1[C@@H]1CC[C@@]2(O)[C@H]3Cc4ccc(O)c5c4[C@@]2(CCN3CC2CC2)[C@H]1O5]

is named 2-[17-(cyclopropylmethyl)-4,5α-epoxy-3,14-dihydroxymorphinan-6β-yl]-6-fluoro-2,3-dihydro-isoindol-1-one.

TABLE 2

| $R^1$ | $R^2$ | $R^3$ | $R^{6a}$ | $R^{6b}$ | $R^{6c}$ | $R^{6d}$ |
|---|---|---|---|---|---|---|
| CPM | OH | OH | — | — | — | — |
| CPM | OH | OH | F | — | — | — |
| CPM | OH | OH | — | F | — | — |
| CPM | OH | OH | — | — | F | — |
| CPM | OH | OH | — | — | — | F |
| CPM | OH | OH | — | F | F | — |
| CPM | OH | OH | F | F | F | F |
| CPM | OH | OH | Cl | — | — | — |
| CPM | OH | OH | — | Cl | — | — |
| CPM | OH | OH | — | — | Cl | — |
| CPM | OH | OH | — | — | — | Cl |
| CPM | OH | OH | — | Cl | Cl | — |
| CPM | OH | OH | Me | — | — | — |
| CPM | OH | OH | — | Me | — | — |
| CPM | OH | OH | — | — | Me | — |
| CPM | OH | OH | — | — | — | Me |
| CPM | OH | OH | — | Me | Me | — |
| CPM | OH | OH | OMe | — | — | — |
| CPM | OH | OH | — | OMe | — | — |
| CPM | OH | OH | — | — | OMe | — |
| CPM | OH | OH | — | — | — | OMe |
| CPM | OH | OH | — | OMe | OMe | — |
| Allyl | OH | OH | — | — | — | — |
| Allyl | OH | OH | F | — | — | — |
| Allyl | OH | OH | — | F | — | — |
| Allyl | OH | OH | — | — | F | — |
| Allyl | OH | OH | — | — | — | F |
| Allyl | OH | OH | — | F | F | — |
| Allyl | OH | OH | F | F | F | F |
| Allyl | OH | OH | Cl | — | — | — |
| Allyl | OH | OH | — | Cl | — | — |
| Allyl | OH | OH | — | — | Cl | — |
| Allyl | OH | OH | — | — | — | Cl |
| Allyl | OH | OH | — | Cl | Cl | — |
| Allyl | OH | OH | Me | — | — | — |
| Allyl | OH | OH | — | Me | — | — |
| Allyl | OH | OH | — | — | Me | — |
| Allyl | OH | OH | — | — | — | Me |
| Allyl | OH | OH | — | Me | Me | — |
| Allyl | OH | OH | OMe | — | — | — |
| Allyl | OH | OH | — | OMe | — | — |
| Allyl | OH | OH | — | — | OMe | — |
| Allyl | OH | OH | — | — | — | OMe |
| Allyl | OH | OH | — | OMe | OMe | — |
| CPM | H | OH | — | — | — | — |
| CPM | H | OH | F | — | — | — |
| CPM | H | OH | — | F | — | — |
| CPM | H | OH | — | — | F | — |
| CPM | H | OH | — | — | — | F |
| CPM | H | OH | — | F | F | — |
| CPM | H | OH | F | F | F | F |
| CPM | H | OH | Cl | — | — | — |
| CPM | H | OH | — | Cl | — | — |
| CPM | H | OH | — | — | Cl | — |
| CPM | H | OH | — | — | — | Cl |
| CPM | H | OH | — | Cl | Cl | — |
| CPM | H | OH | Me | — | — | — |
| CPM | H | OH | — | Me | — | — |
| CPM | H | OH | — | — | Me | — |
| CPM | H | OH | — | — | — | Me |
| CPM | H | OH | — | Me | Me | — |
| CPM | H | OH | OMe | — | — | — |
| CPM | H | OH | — | OMe | — | — |
| CPM | H | OH | — | — | OMe | — |
| CPM | H | OH | — | — | — | OMe |
| CPM | H | OH | — | OMe | OMe | — |
| Allyl | H | OH | — | — | — | — |
| Allyl | H | OH | F | — | — | — |
| Allyl | H | OH | — | F | — | — |
| Allyl | H | OH | — | — | F | — |
| Allyl | H | OH | — | — | — | F |
| Allyl | H | OH | — | F | F | — |
| Allyl | H | OH | F | F | F | F |
| Allyl | H | OH | Cl | — | — | — |
| Allyl | H | OH | — | Cl | — | — |
| Allyl | H | OH | — | — | Cl | — |
| Allyl | H | OH | — | — | — | Cl |
| Allyl | H | OH | — | Cl | Cl | — |
| Allyl | H | OH | Me | — | — | — |
| Allyl | H | OH | — | Me | — | — |
| Allyl | H | OH | — | — | Me | — |
| Allyl | H | OH | — | — | — | Me |
| Allyl | H | OH | — | Me | Me | — |
| Allyl | H | OH | OMe | — | — | — |
| Allyl | H | OH | — | OMe | — | — |
| Allyl | H | OH | — | — | OMe | — |
| Allyl | H | OH | — | — | — | OMe |
| Allyl | H | OH | — | OMe | OMe | — |

Among the compounds represented by Formula (I), specific examples of the compounds wherein —X— is ethylene or vinylene, Y is —C(=O)—, $R^{10}$, $R^{13}$ and $R^{14}$ are hydrogen, $R^{11}$ and $R^{12}$ are bound to form —O—, and two $R^5$s bound to adjacent carbon atoms, respectively, cooperatively form specific fused ring, that is, the compounds represented by the Formula (Ic) or Formula (Ic') below are shown in Table 3.

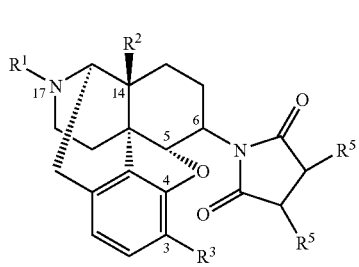
(Ic)

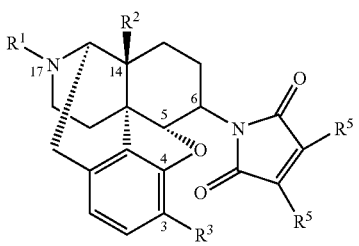
(Ic')

Among the compounds represented by Formula (Ic'), the compound wherein R¹ is cyclopropylmethyl, R² and R³ are hydroxy, two R⁵s bound to adjacent carbon atoms, respectively, cooperatively form cyclohexeno, and the configuration of the bond at the 6-position is β, that is, the compound of the following formula:

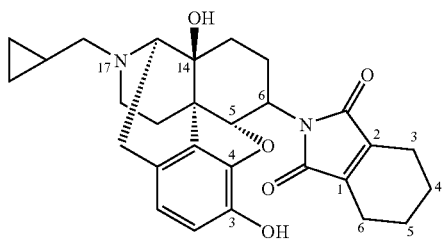 [SMILES: O=C1C2=C(CCCC2)C(=O)N1C1CC[C@@]2(O)[C@H]3Cc4ccc(O)c5c4[C@@]2(CCN3CC2CC2)[C@H]1O5]

is named N-(17-cyclopropylmethyl-4,5α-epoxy-3,14-dihydroxymorphinan-6β-yl)-3,4,5,6-tetrahydrophthalimide.

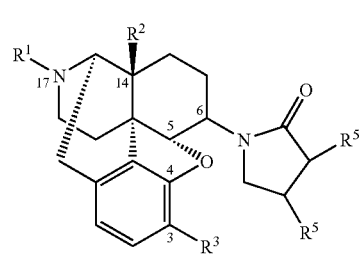
(Id)

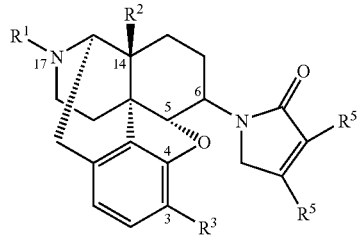
(Id')

Among the compounds represented by Formula (Id'), the compound wherein R¹ is cyclopropylmethyl, R² and R³ are hydroxy, two R⁵s bound to adjacent carbon atoms, respectively, cooperatively form cyclohexeno, and the configuration of the bond at the 6-position is β, that is, the compound of the following formula:

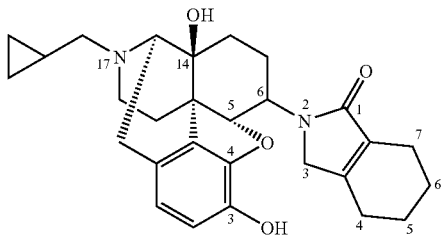 [SMILES: O=C1C2=C(CCCC2)CN1C1CC[C@@]2(O)[C@H]3Cc4ccc(O)c5c4[C@@]2(CCN3CC2CC2)[C@H]1O5]

is named N-(17-cyclopropylmethyl-4,5α-epoxy-3,14-dihydroxymorphinan-6β-yl)-2,3,4,5,6,7-hexahydro-isoindol-1-one.

TABLE 3

| Formula | R¹ | R² | R³ | R⁵ |
|---|---|---|---|---|
| Ic | CPM | OH | OH | Cyclopropano |
| Ic | CPM | OH | OH | Cyclopentano |
| Ic | CPM | OH | OH | Cyclohexano |
| Ic' | CPM | OH | OH | Cyclohexeno |
| Ic' | CPM | OH | OH | Pyrido |
| Ic | Allyl | OH | OH | Cyclopropano |
| Ic | Allyl | OH | OH | Cyclopentano |
| Ic | Allyl | OH | OH | Cyclohexano |
| Ic' | Allyl | OH | OH | Cyclohexeno |
| Ic' | Allyl | OH | OH | Pyrido |

TABLE 4

| Formula | R¹ | R² | R³ | R⁵ |
|---|---|---|---|---|
| Id | CPM | OH | OH | Cyclopropano |
| Id | CPM | OH | OH | Cyclopentano |
| Id | CPM | OH | OH | Cyclohexano |
| Id' | CPM | OH | OH | Cyclohexeno |
| Id' | CPM | OH | OH | Pyrido |
| Id | Allyl | OH | OH | Cyclopropano |
| Id | Allyl | OH | OH | Cyclopentano |
| Id | Allyl | OH | OH | Cyclohexano |
| Id' | Allyl | OH | OH | Cyclohexeno |
| Id' | Allyl | OH | OH | Pyrido |

Among the compounds represented by Formula (I), specific examples of the compounds wherein —X— is propylene or propenylene, Y is valence bond, $R^{10}$, $R^{13}$ and $R^{14}$ are hydrogen, $R^{11}$ and $R^{12}$ are bound to form —O—, and two $R^5$s bound to adjacent carbon atoms, respectively, cooperatively form specific fused ring, that is, the compounds represented by the Formula (Id) or Formula (Id') below are shown in Table 4.

Among the compounds represented by Formula (I), specific examples of the compounds wherein —X— is ethylene or vinylene which is non-substituted or substituted by $R^{5a}$ and/or $R^{5b}$ ($R^{5a}$ and $R^{5b}$ have the same meanings as the above-described $R^5$), Y is —C(=O)—, $R^{10}$, $R^{13}$ and $R^{14}$ are hydrogen, $R^{11}$ and $R^{12}$ are bound to form —O—, that is, the compounds represented by the Formula (Ie) or Formula (Ie') below are shown in Table 5.

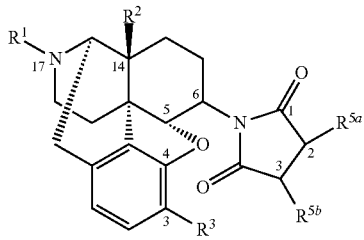

(Ie)

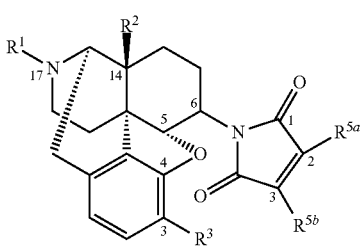

(Ie′)

Among the compounds represented by Formula (Ie), the compound wherein $R^1$ is cyclopropylmethyl, $R^2$ and $R^3$ are hydroxy, $R^{5a}$ is ethylidene, and the configuration of the bond at the 6-position is β, that is, the compound of the following formula:

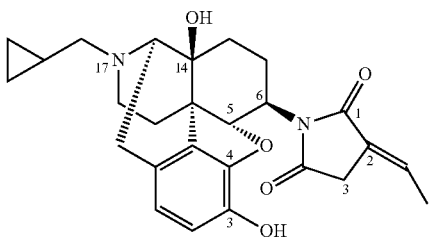 [SMILES: C/C=C1\CC(=O)N([C@@H]2CC[C@@]3(O)[C@H]4Cc5ccc(O)c6c5[C@@]3(CCN4CC3CC3)[C@H]2O6)C1=O]

is named N-[17-(cyclopropylmethyl)-4,5α-epoxy-3,14-dihydroxymorphinan-6β-yl]-2-ethylidene succinic imide.

TABLE 5

| Formula | $R^1$ | $R^2$ | $R^3$ | $R^{5a}$ | $R^{5b}$ |
|---|---|---|---|---|---|
| Ie | CPM | OH | OH | — | — |
| Ie | CPM | OH | OH | methylidene | — |
| Ie | CPM | OH | OH | ethylidene | — |
| Ie | CPM | OH | OH | propylidene | — |
| Ie | CPM | OH | OH | butylidene | — |
| Ie | CPM | OH | OH | cyclohexylmethylidene | — |
| Ie | CPM | OH | OH | benzylidene | — |
| Ie | CPM | OH | OH | phenethylidene | — |
| Ie | CPM | OH | OH | methyl | — |
| Ie | CPM | OH | OH | ethyl | — |
| Ie | CPM | OH | OH | propyl | — |
| Ie | CPM | OH | OH | butyl | — |
| Ie | CPM | OH | OH | cyclohexylmethyl | — |
| Ie | CPM | OH | OH | benzyl | — |
| Ie | CPM | OH | OH | p-methyl-benzyl | — |
| Ie | CPM | OH | OH | p-fluoro-benzyl | — |
| Ie | CPM | OH | OH | p-chloro-benzyl | — |
| Ie | CPM | OH | OH | p-trifluoromethoxy-benzyl | — |
| Ie | CPM | OH | OH | phenethyl | — |
| Ie | CPM | OH | OH | phenoxy | — |
| Ie | CPM | OH | OH | p-methyl-phenoxy | — |
| Ie | CPM | OH | OH | p-fluoro-phenoxy | — |
| Ie | CPM | OH | OH | p-chloro-phenoxy | — |
| Ie | CPM | OH | OH | phenyl | — |
| Ie | CPM | OH | OH | phenyl | phenyl |

TABLE 5-continued

| Formula | $R^1$ | $R^2$ | $R^3$ | $R^{5a}$ | $R^{5b}$ |
|---|---|---|---|---|---|
| Ie′ | CPM | OH | OH | — | — |
| Ie′ | CPM | OH | OH | phenyl | — |
| Ie′ | CPM | OH | OH | phenyl | phenyl |
| Ie′ | CPM | OH | OH | methyl | — |
| Ie′ | CPM | OH | OH | methyl | methyl |
| Ie | Allyl | OH | OH | — | — |
| Ie | Allyl | OH | OH | methylidene | — |
| Ie | Allyl | OH | OH | ethylidene | — |
| Ie | Allyl | OH | OH | propylidene | — |
| Ie | Allyl | OH | OH | butylidene | — |
| Ie | Allyl | OH | OH | cyclohexylmethylidene | — |
| Ie | Allyl | OH | OH | benzylidene | — |
| Ie | Allyl | OH | OH | phenethylidene | — |
| Ie | Allyl | OH | OH | methyl | — |
| Ie | Allyl | OH | OH | ethyl | — |
| Ie | Allyl | OH | OH | propyl | — |
| Ie | Allyl | OH | OH | butyl | — |
| Ie | Allyl | OH | OH | cyclohexylmethyl | — |
| Ie | Allyl | OH | OH | benzyl | — |
| Ie | Allyl | OH | OH | p-methyl-benzyl | — |
| Ie | Allyl | OH | OH | p-fluoro-benzyl | — |
| Ie | Allyl | OH | OH | p-chloro-benzyl | — |
| Ie | Allyl | OH | OH | p-trifluoromethoxy-benzyl | — |
| Ie | Allyl | OH | OH | phenethyl | — |
| Ie | Allyl | OH | OH | phenoxy | — |
| Ie | Allyl | OH | OH | p-methyl-phenoxy | — |
| Ie | Allyl | OH | OH | p-fluoro-phenoxy | — |
| Ie | Allyl | OH | OH | p-chloro-phenoxy | — |
| Ie | Allyl | OH | OH | phenyl | — |
| Ie | Allyl | OH | OH | phenyl | phenyl |
| Ie′ | Allyl | OH | OH | — | — |
| Ie′ | Allyl | OH | OH | phenyl | — |
| Ie′ | Allyl | OH | OH | phenyl | phenyl |
| Ie′ | Allyl | OH | OH | methyl | — |
| Ie′ | Allyl | OH | OH | methyl | methyl |

Among the compounds represented by Formula (I), specific examples of the compounds wherein —X— is propylene or propenylene which is non-substituted or substituted by $R^{5a}$ and/or $R^{5b}$ ($R^{5a}$ and $R^{5b}$ have the same meanings as the above-described $R^5$), Y is valence bond, $R^{10}$, $R^{13}$ and $R^{14}$ are hydrogen, $R^{11}$ and $R^{12}$ are bound to form —O—, that is, the compounds represented by the Formula (If) or Formula (If′) below are shown in Table 6.

(If)

(If′)

Among the compounds represented by Formula (If), the compound wherein $R^1$ is cyclopropylmethyl, $R^2$ and hydroxy, $R^{5a}$ is benzyl, and the configuration of the bond at the 6-position is β, that is, the compound of the following formula:

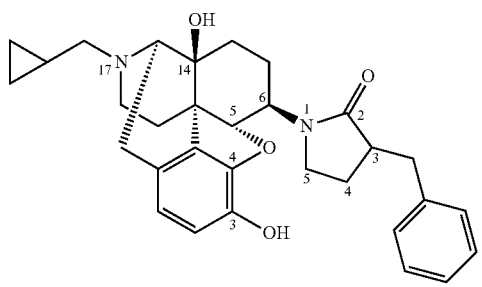 [SMILES: O=C1C(Cc2ccccc2)CCN1[C@@H]1CC[C@@]2(O)[C@H]3Cc4ccc(O)c5c4[C@@]2(CCN3CC2CC2)[C@H]1O5]

is named 3-benzyl-1-[17-(cyclopropylmethyl)-4,5α-epoxy-3,14-dihydroxymorphinan-6β-yl]pyrrolidine-2-one.

TABLE 6

| Formula | $R^1$ | $R^2$ | $R^3$ | $R^{5a}$ | $R^{5b}$ |
|---|---|---|---|---|---|
| If | CPM | OH | OH | — | — |
| If | CPM | OH | OH | methylidene | — |
| If | CPM | OH | OH | ethylidene | — |
| If | CPM | OH | OH | propylidene | — |
| If | CPM | OH | OH | butylidene | — |
| If | CPM | OH | OH | cyclohexylmethylidene | — |
| If | CPM | OH | OH | benzylidene | — |
| If | CPM | OH | OH | phenethylidene | — |
| If | CPM | OH | OH | Methyl | — |
| If | CPM | OH | OH | Ethyl | — |
| If | CPM | OH | OH | Propyl | — |
| If | CPM | OH | OH | Butyl | — |
| If | CPM | OH | OH | cyclohexylmethyl | — |
| If | CPM | OH | OH | Benzyl | — |
| If | CPM | OH | OH | p-methyl-benzyl | — |
| If | CPM | OH | OH | p-fluoro-benzyl | — |
| If | CPM | OH | OH | p-chloro-benzyl | — |
| If | CPM | OH | OH | p-trifluoromethoxy-benzyl | — |
| If | CPM | OH | OH | phenethyl | — |
| If | CPM | OH | OH | Phenoxy | — |
| If | CPM | OH | OH | p-methyl-phenoxy | — |
| If | CPM | OH | OH | p-fluoro-phenoxy | — |
| If | CPM | OH | OH | p-chloro-phenoxy | — |
| If | CPM | OH | OH | Phenyl | — |
| If | CPM | OH | OH | Phenyl | phenyl |
| If' | CPM | OH | OH | — | — |
| If' | CPM | OH | OH | Phenyl | — |
| If' | CPM | OH | OH | Phenyl | phenyl |
| If' | CPM | OH | OH | Methyl | — |
| If' | CPM | OH | OH | Methyl | methyl |
| If | Allyl | OH | OH | — | — |
| If | Allyl | OH | OH | methylidene | — |
| If | Allyl | OH | OH | ethylidene | — |
| If | Allyl | OH | OH | propylidene | — |
| If | Allyl | OH | OH | butylidene | — |
| If | Allyl | OH | OH | cyclohexylmethylidene | — |
| If | Allyl | OH | OH | benzylidene | — |
| If | Allyl | OH | OH | phenethylidene | — |
| If | Allyl | OH | OH | Methyl | — |
| If | Allyl | OH | OH | Ethyl | — |
| If | Allyl | OH | OH | Propyl | — |
| If | Allyl | OH | OH | Butyl | — |
| If | Allyl | OH | OH | cyclohexylmethyl | — |
| If | Allyl | OH | OH | Benzyl | — |
| If | Allyl | OH | OH | p-methyl-benzyl | — |
| If | Allyl | OH | OH | p-fluoro-benzyl | — |
| If | Allyl | OH | OH | p-chloro-benzyl | — |
| If | Allyl | OH | OH | p-trifluoromethoxy-benzyl | — |
| If | Allyl | OH | OH | phenethyl | — |
| If | Allyl | OH | OH | Phenoxy | — |
| If | Allyl | OH | OH | p-methyl-phenoxy | — |
| If | Allyl | OH | OH | p-fluoro-phenoxy | — |
| If | Allyl | OH | OH | p-chloro-phenoxy | — |

TABLE 6-continued

| Formula | $R^1$ | $R^2$ | $R^3$ | $R^{5a}$ | $R^{5b}$ |
|---|---|---|---|---|---|
| If | Allyl | OH | OH | Phenyl | — |
| If | Allyl | OH | OH | Phenyl | phenyl |
| If' | Allyl | OH | OH | — | — |
| If' | Allyl | OH | OH | Phenyl | — |
| If' | Allyl | OH | OH | Phenyl | phenyl |
| If' | Allyl | OH | OH | Methyl | — |
| If' | Allyl | OH | OH | Methyl | methyl |

The above-described various morphinan derivatives and pharmaceutically acceptable acid addition salts thereof may be used as the effective ingredient of the analgesic individually, or two or more of these may be used in combination.

Among the morphinan derivatives having a nitrogen-containing heterocyclic group represented by the above-described Formula (I) and the pharmaceutically acceptable acid addition salts thereof, those wherein both $R^{13}$ and $R^{14}$ are hydrogen, that is, those represented by Formula (Ig) below (wherein $R^1$, $R^2$, $R^3$, $R^5$, $R^{10}$, $R^{11}$, $R^{12}$, k, X and Y represent the same meanings as described above) and pharmaceutically acceptable acid addition salts thereof may be produced by the methods described in International Patent Publication No.: WO2004/033457 (European Patent Publication EP 1 555 266 A1), Tetrahedron. 50, 9757 (1994) and so on.

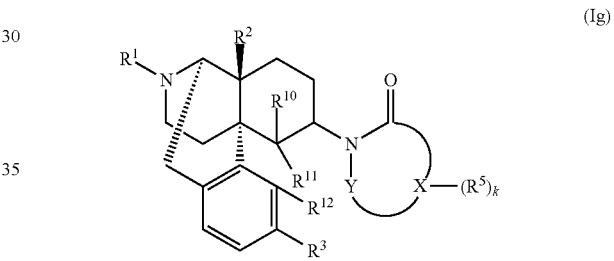

(Ig)

Among the morphinan derivatives having a nitrogen-containing heterocyclic group represented by the above-described Formula (I) and the pharmaceutically acceptable acid addition salts thereof, those wherein both $R^{13}$ and $R^{14}$ are $R^{13'}$ and $R^{14'}$ (wherein $R^{13'}$ and $R^{14'}$ cooperatively represent oxo, or $R^{13'}$ is hydrogen and $R^{14'}$ is hydroxy, $C_1$-$C_5$ alkoxy or $C_1$-$C_5$ alkanoyloxy), that is, those represented by Formula (Ih) below (wherein $R^1$, $R^2$, $R^3$, $R^5$, $R^{10}$, $R^{11}$, $R^{12}$, k, X and Y represent the same meanings as described above) and pharmaceutically acceptable acid addition salts thereof may be produced, as shown in Scheme 1 below, by directly oxidizing the benzyl position of the morphinan derivative having a nitrogen-containing heterocyclic group of Formula (Ig) (wherein $R^1$, $R^2$, $R^3$, $R^5$, $R^{10}$, $R^{11}$, $R^{12}$, k, X and Y represent the same meanings as described above) described above obtained by the method described in WO2004/033457 (EP 1555266 A1), or by oxidizing the benzyl position of the morphinan derivative represented by Formula (IIa) (wherein $R^1$, $R^2$, $R^3$, $R^{10}$, $R^{11}$, $R^{12}$ represent the same meanings as described above, . . . Q represents oxo or benzylamino) to obtain the intermediate represented by Formula (IIb) (wherein $R^1$, $R^2$, $R^3$, $R^{10}$, $R^{11}$, $R^{12}$, $R^{13'}$, $R^{14'}$ and . . . Q represent the same meanings as described above), and then applying thereto the method described in WO2004/033457 (EP 1555266 A1) mentioned above. In the oxidation of the benzyl position, the hydroxy group or the oxo group may be directly introduced, or after the oxo group is introduced, it may be reduced to hydroxyl group. Further, depending on the types of the substituents, protection and deprotection steps may be added as required.

ing carbonyl compounds may be employed, hydride reducing agents such as sodium borohydride and lithium aluminum hydride may preferably be employed.

Scheme 1

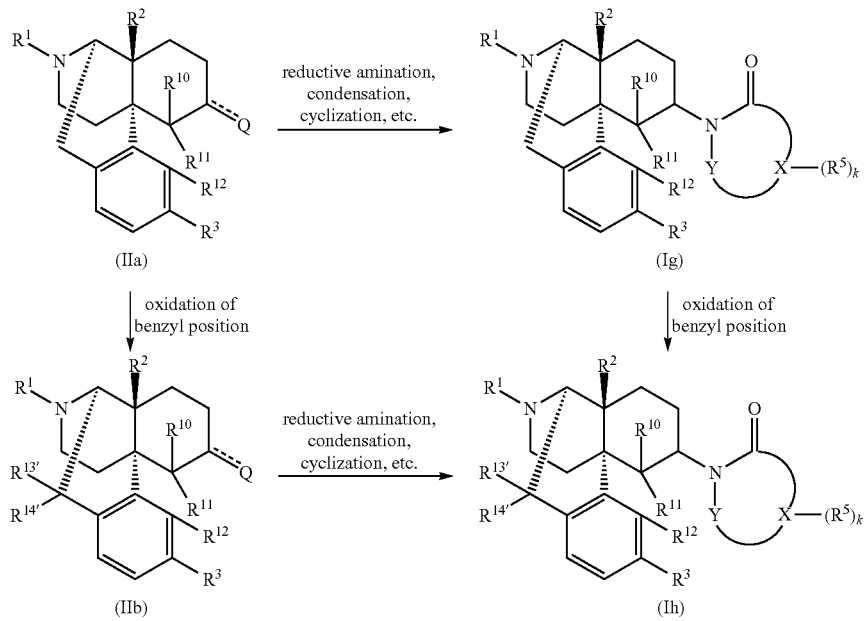

In the oxidation step, although any oxidizing agent which may usually be used for the oxidation of benzyl position may be employed, in case of introducing hydroxyl group, for example, manganese (III) salts such as manganese (III) acetate; lead compounds such as lead tetraacetate; organic peroxides such as t-butyl hydroperoxide and benzoyl peroxide; cerium compounds such as cerium (IV) ammonium nitrate (CAN); and oxygen may be used as the oxidizing agent. Among these, by using cerium (IV) ammonium nitrate, the α-hydroxy compound may be selectively obtained in some cases, so that it is useful. By using an oxidizing agent which contains an organic acid such as acetic acid in its chemical structure, alkanoyl group such as acetoxy may be effectively introduced in some cases.

In cases where an oxo group is to be introduced, permanganates such as potassium permanganate; manganese compounds such as manganese dioxide; chromium compounds such as chromium oxide and sodium chromate; selenium compounds such as selenium dioxide; periodates such as sodium periodate; quinones such as DDQ; silver compounds such as silver oxide; cerium compounds such as cerium (IV) ammonium nitrate (CAN); halogens (chlorine, bromine and iodine); oxygen; hydrogen peroxide; and the like may be used.

The reaction conditions such as reaction solvent, reaction temperature, reaction time, substrate concentration and equivalence ratio of the reagents may be appropriately selected depending on the oxidizing agent used, and in case of using a cerium compound such as cerium (IV) ammonium nitrate (CAN), for example, the desired compound may be obtained with high yield by reacting 4 equivalence of the oxidizing agent with respect to the substrate in a mixed solvent of acetonitrile/water at room temperature.

In cases where the oxo group is reduced to hydroxyl group, although any ordinary reducing agent which is used for reduc- The reaction conditions such as reaction solvent, reaction temperature, reaction time, substrate concentration and equivalence ratio of the reagents may be appropriately selected depending on the reducing agent used, and in case of using sodium borohydride, for example, the desired compound may be obtained at a high yield by carrying out the reaction in an alcoholic solvent such as methanol at room temperature. In cases where the hydroxyl group is generated via the reduction step of oxo group, compounds having β-configuration may be selectively obtained opposite to the cases where the hydroxyl group is directly attached.

Conversion of the hydroxy compound into the alkoxy compound or alkanoyloxy compound may be carried out under ordinary etherification or acylation conditions. Conversion into an acid addition salt may be carried out by mixing the compound with a pharmaceutically acceptable acid in water or in an organic solvent, and carrying out concentration to dryness, reprecipitation, recrystallization and/or the like.

The fact that the morphinan derivatives having a nitrogen-containing heterocyclic group represented by Formula (I) and the pharmaceutically acid addition salts thereof are effective for the therapy of pain may be confirmed by showing the actions of the compounds to reduce the behavior induced by pain in animal models. For example, the reported testing methods utilizing the behavior induced by pain in animal models include mouse acetic acid writhing method (Life Sci., vol 65, 1685-93 (1996)) for treating acute pain, $PGF_2\alpha$-induced allodynia model method in which pain is induced, for which morphine is ineffective (Pain. Vol 50, 223-229 (1992)), rat Chung model method (Pain. Vol 50, 355-363 (1992)), mouse Seltzer model method (Pain. Vol 76, 215-222 (1998)) and diabetic induced neuropathic pain model method (Pain. Vol 80, 391-398)). $PGF_2\alpha$-induced allodynia model has also been reported as an animal model which induces allodynia that is a characteristic symptom to the patients suffering from chronic pain (PAIN RESEARCH., vol 7, 129-134 (1992), Pain. Vol 50, 223-229 (1992)).

As will be shown in Examples 1 to 5 below, the morphinan derivatives having a nitrogen-containing heterocyclic group represented by Formula (I) and the pharmaceutically acid addition salts thereof exhibited highly potent analgesic activities when evaluated by the acetic acid writhing method. Further, it was confirmed that they have analgesic activities in $PGF_2\alpha$-induced allodynia model, rat Chung model, mouse Seltzer model, diabetic induced neuropathic pain model, and in evaluation of activity to relieve cystalgia caused by hyperextension of bladder using myoelectric activity of external oblique abdominal muscle as index, so that the derivatives may be widely applied to various pain ranging from acute pain to chronic pain. The analgesic may be applied to acute pain including, for example, pain due to injuries such as fracture and incised wound; pain due to inflammation such as appendicitis; and postoperative pain; and to chronic pain including neuropathic pain such as cancer pain, herpes zoster pain, postherpetic neuralgia, trigeminal neuralgia; and pain due to diabetic neuralgia, causalgia, phantom limb pain. In addition, they may be applied to deep pain and visceral pain such as headache, abdominal pain, back pain, chronic pelvic pain syndrome, cystalgia, pain due to vaginitis, (chronic) prostatitis, endometriosis, myoma of the uterus, urolithiasis, urethral calculus, cystitis, urethritis, urinary tract infection or due to interstitial cystitis, colicky pain due to digestive organ disease, pelvic pain, urologic diseases pain; and pain in gynecologic field such as pain due to dysmenorrhea; and psychogenic pain. The analgesic may be used for mammals (e.g., mouse, rat, hamster, rabbit, cat, dog, bovine, sheep, monkey and human).

The analgesic may be administered alone or in combination with other one or more drugs used for the therapy or prevention of diseases, or for alleviation or inhibition of symptoms. When the analgesic is administered in combination with one or more other drugs, the analgesic and the drug(s) may be separately administered or may be administered after being mixed together. Examples of such drugs include COX-1 and/or COX-2 inhibitors which are nonsteroidal anti-inflammatory drugs (NSAIDs), such as aspirin, indomethacin, diclofenac, ibuprofen, acetaminophen, acetylsalicylic acid, ketoprofen, piroxicam, mefenamic acid, tiaramide, naproxen, Loxonin, oxaprozin, zaltoprofen, etodolac, meloxicam, lornoxicam, amproxicam, celecoxib, rofecoxib, valdecoxib, lumiracoxib and licofelone; opioid analgesics such as codeine, morphine, dihydrocodeine, hydrocodone, hydromorphone, oxycodone, fentanyl, buprenorphine, butorphanol, nalbuphine, pentazocine, levorphanol, methadone, pethidine, tramadol and oxymorphone; other analgesics such as gabapentin, pregabalin and baclofen; anesthetic drugs such as halothane, lidocaine, etidocaine, ropivacaine, chloroprocaine, bupivacaine and propofol; benzodiazepine drugs such as diazepam, chlordiazepoxide, alprazolam and lorazepam; skeletal muscle relaxants such as carisoprodol, Robaxisal and Dantrium; migraine-abortive agents such as ergotamine, elitriptan, sumatriptan, rizatriptan, zolmitriptan and naratriptan; anticonvulsants such as carbamazepine, clonazepam, topiramate, phenyloin, valproic acid, zonisamide and oxcarbazepine; antidepressants such as amitriptyline, nortriptyline, tryptanol, amoxapine, imipramine, paroxetine, fluvoxamine, milnacipran and duloxetine; corticosteroids such as prednisolone, dexamethasone and betamethasone; NMDA antagonists such as dextromethorphan, ketamine, memantine, amantadine and ifenprodil; vanilloid agonists and antagonists such as capsaicin and resiniferatoxin; calcium channel blockers such as ziconotide; potassium channel openers such as flupirtine and retigabine; serotonin receptor antagonists; sodium channel blockers; cannabinoids; and toxins such as botulinum toxin and tetrodotoxin, but these drugs are examples and should not be interpreted in any way to restrict the scope of this disclosure.

When using the analgesic as a pharmaceutical, the pharmaceutical may be the free base or a salt thereof alone, or the pharmaceutical may optionally be admixed with one or more additives such as vehicles, stabilizers, preservatives, buffering agents, solubilizers, emulsifiers, diluents and isotonic agents. The formulations may be prepared by usual methods appropriately using the carriers for each type of formulation. The administration form include formulations for oral administration such as tablets, capsules, granules, powders and syrups; formulations for parenteral administration such as injection solutions, suppositories and liquids; and formulations for topical administration such as ointments, creams and patches.

The analgesic may preferably contain the above-described effective ingredient in an amount of 0.00001 to 90% by weight, more preferably 0.0001 to 70% by weight. Although the administration dose may be appropriately selected depending on the symptom, age, body weight, and administration method and the like, the dose of the effective component per adult per day may be 0.1 µg to 1 g in case of administration by injection, and may be 1 µg to 10 g in case of oral administration. Each dose may be administered in one time or dividedly in several times.

Representative examples will now be described in detail.

Compound 1 [1-(17-cyclopropylmethyl-4,5α-epoxy-3,14-dihydroxy-morphinan-6β-yl)pyrrolidine-2-one-hydrochloric acid salt], Compound 2 [1-(17-cyclopropylmethyl-4,5α-epoxy-3,14-dihydroxy-morphinan-6α-yl)pyrrolidine-2-one-hydrochloric acid salt], Compound 3 [1-(17-cyclopropylmethyl-4,5α-epoxy-3,14-dihydroxy-morphinan-6β-yl)-3-benzyl-pyrrolidine-2-one.tartaric acid salt], Compound 4 [1-(17-cyclopropylmethyl-4,5α-epoxy-3,14-dihydroxymorphinan-6α-yl)-3-benzyl-pyrrolidine-2-one (diastereomer mixture).tartaric acid salt], Compound [2-(17-cyclopropylmethyl-4,5α-epoxy-3,14-dihydroxy-morphinan-6β-yl)-2,3-dihydroisoindol-1-one.tartaric acid salt], Compound 6 [N-(17-cyclopropylmethyl-4,5α-epoxy-3,14-dihydroxy-morphinan-6β-yl)-2-butylidene succinic imide.tartaric acid salt], Compound 7 [N-(17-allyl-4,5α-epoxy-3,14-dihydroxymorphinan-6β-yl)-4-fluorophthalimide.tartaric acid salt], Compound 8 [N-(17-allyl-4,5α-epoxy-3,14-dihydroxy-morphinan-6α-yl)-3-fluorophthal-imide.tartaric acid salt], Compound 9 [N-(17-allyl-4,5α-epoxy-3,14-dihydroxymorphinan-6α-yl)-phthalimide.tartaric acid salt], Compound 10 [N-(17-cyclopropylmethyl-4,5α-epoxy-3,14-dihydroxymorphinan-6β-yl)-phthalimide.hydrochloric acid salt], Compound 10f [N-(17-cyclopropylmethyl-4,5α-epoxy-3,14-dihydroxy-morphinan-6β-yl)-phthalimide], Compound 11 [N-(17-cyclopropylmethyl-4,5α-epoxy-3,14-dihydroxy-morphinan-6β-yl)-4-methylphthalimide.hydrochloric acid salt], Compound 12 [N-(17-cyclopropylmethyl-4,5α-epoxy-3,14-dihydroxy-morphinan-6β-yl)-4-chlorophthalimide.tartaric acid salt], Compound 13 [N-(17-cyclopropylmethyl-4,5α-epoxy-3,14-dihydroxy-morphinan-6β-yl)-4-fluorophthalimide.tartaric acid salt], Compound 14 [N-(17-cyclopropylmethyl-4,5α-epoxy-3,14-dihydroxy-morphinan-6β-yl)-3-fluorophthalimide.tartaric acid salt], Compound 15 [N-(17-cyclopropylmethyl-4,5α-epoxy-3,14-dihydroxy-morphinan-6β-yl)-3-methylphthalimide.tartaric acid salt], Compound 16 [N-(17-cyclopropylmethyl-4,5α-epoxy-3,14-dihydroxy-morphinan-6β-yl)naphthalenedicarboxylic imide.hydrochloric acid salt], Compound 17 [N-[17-(cyclopropylmethyl)-4,5α-epoxy-3,14-dihydroxymorphinan-6β-yl]]-4,5-dichlorophthalimide.tartaric acid salt], Compound 18 [N-(17-cyclopropylmethyl-4,5α-epoxy-3,14-dihydroxy-morphinan-6β-yl)-phthalimide.tartaric acid salt], Compound 19 [N-(17-cyclopropylmethyl-4,5α-epoxy-3,14-dihydroxy-morphinan-6β-yl)-3,4,5,6-tetrahydrophthalimide.tartaric acid salt], Compound 20 [17-cyclopropylmethyl-4,5α-epoxy-6β-(pyrrolidine-1-yl)-morphinan-3,14-diol.tartaric acid salt] and Compound 21 [N-(17-cyclopropylmethyl-4,5α-epoxy-3,14-dihydroxy-morphinan-6β-yl)-succinic imide.tartaric acid salt] used in Examples 1 to 5 were synthesized by the methods described in Examples 46, 34, 48-2, 35, 28, 24-2, 58, 63, 64, 11, 12, 15, 16, 17, 18, 19, 55, 66, 77, 111 and 20-2 of International Patent Publication No. WO2004/033457 (European Patent Publication No.: EP 1 555 266 A1).

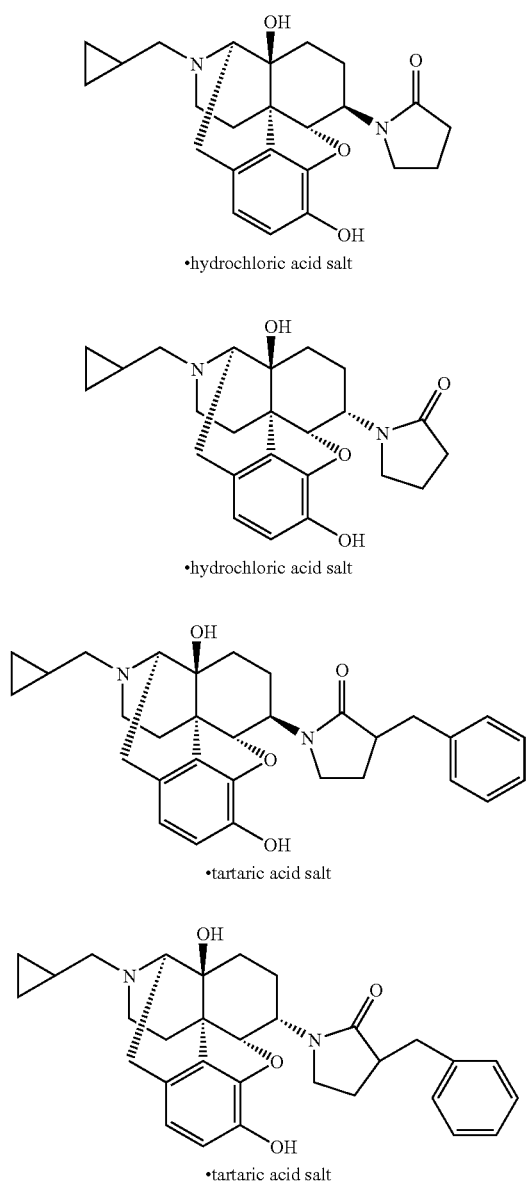

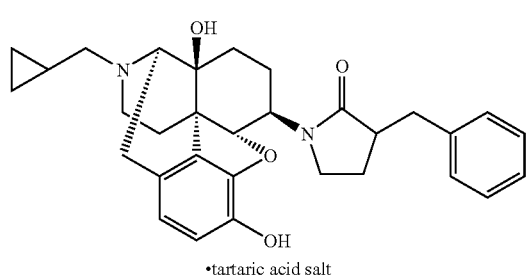

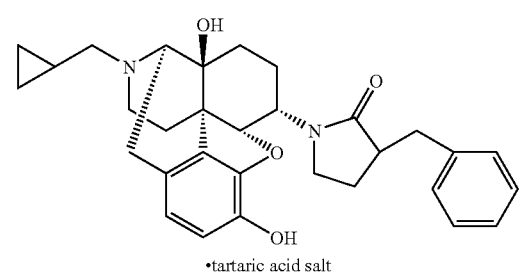

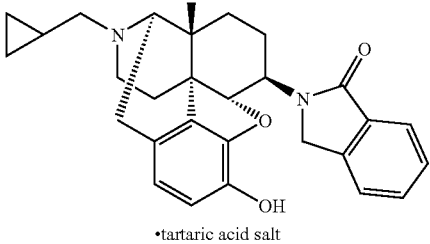

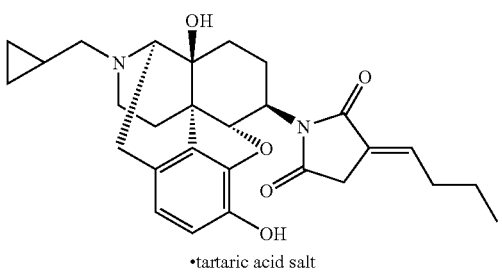

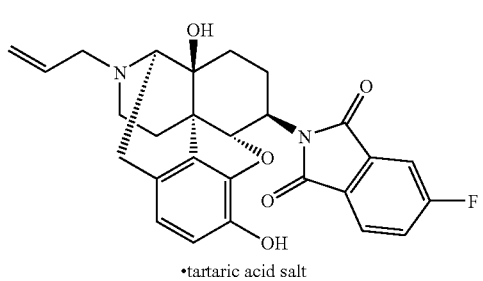

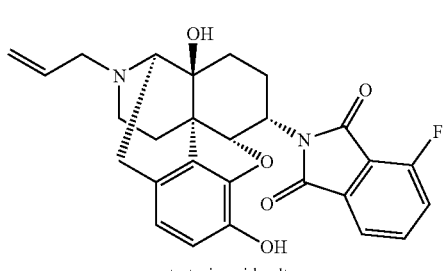

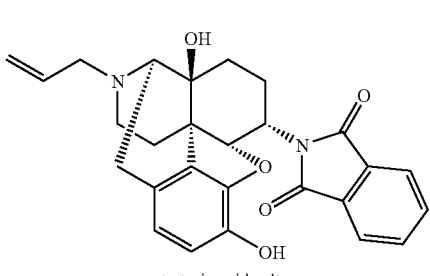

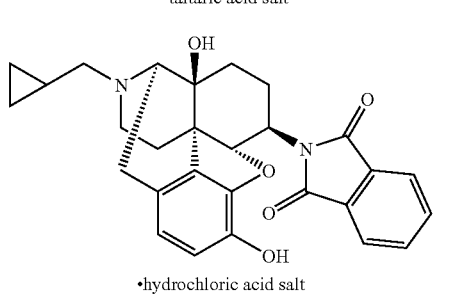

-continued

Reference Example 1

Synthesis of N-(17-cyclopropylmethyl-4,5α-epoxy-3,14-dihydroxy-morphinan-6β-yl)-maleic imide.tartaric acid salt (Compound 22)

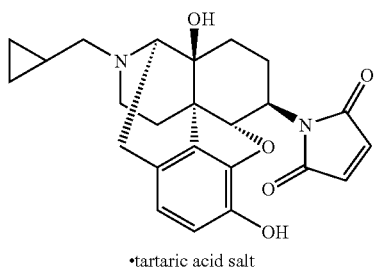

·tartaric acid salt

In DMF (30 mL), 800 mg (2.34 mmol) of 6β-naltrexamine was dissolved, and 252 mg (2.57 mmol) of maleic anhydride and 0.48 mL (3.50 mmol) of triethylamine were added thereto, followed by stirring the resulting mixture at room temperature for 1.5 hours. To the mixture, 0.53 mL (8.18 mmol) of methanesulfonic acid was added, and the resulting mixture was stirred at 120° C. for 8 hours. After allowing the reaction solution to cool to room temperature, saturated aqueous sodium hydrogen carbonate solution was added and the resulting mixture was extracted with ethyl acetate. Organic layers were combined, washed with water and saturated brine, dried over anhydrous magnesium sulfate, and concentrated to obtain a crude product. The obtained crude product was purified by silica gel column chromatography to obtain 141 mg (yield: 14%) of the free form of the captioned Compound 22, and the obtained compound was converted to tartaric acid salt to obtain the captioned Compound 22.

$^1$H-NMR (ppm) (400 MHz, CDCl$_3$) 6.70-6.75 (3H, m), 6.61 (1H, d, J=8.0 Hz), 5.02 (1H, d, J=8.3 Hz), 3.8-3.9 (1H, m), 3.08 (1H, d, J=5.6 Hz), 3.04 (1H, d, J=18.3 Hz), 2.6-2.7 (3H, m), 2.3-2.4 (3H, m), 2.12 (1H, dt, J=12.0, 3.6 Hz), 1.4-1.7 (4H, m), 0.8-0.9 (1H, m), 0.5-0.6 (2H, m), 0.1-0.2 (2H, m) (free form)

Mass (ESI): 423 (M+1)

Example 1

Analgesic Activity Test by Mouse Acetic Acid Writhing Method

To each male ddY mouse, each test compound or the vehicle was subcutaneously administered in an administration volume of 0.1 mL/10 g body weight. Fifteen minutes later, 0.1 mL/10 g body weight of aqueous 0.6% (v/v) acetic acid solution was intraperitoneally administered. From 10 minutes after the administration of the acetic acid solution, the number of writhing response (i.e., the behavior to bend the body backward and/or twist the body) during 10 minutes was counted, and the analgesic activity was evaluated based on the number of writhing response. The ED50 value was evaluated by calculation of the dosage of test compounds to halve the number of writhing response which was observed in vehicle administration. 10% Aqueous dimethylsulfoxide (DMSO) was used as a vehicle for test compounds 1, 2, 3, 4, 5, 6, 7, 8, 9, 10, 11, 12, 13, 14, 15, 16, 17, 18, 19, 20, 21 and 22. 0.1% Citric acid/aqueous 5% xylitol was used as a vehicle for test compounds 10f. The results are shown in Table 7 below.

TABLE 7

| Test Compound | ED50 (mg/kg) |
| --- | --- |
| Compound 1 | 2.62 |
| Compound 2 | 0.95 |
| Compound 3 | 0.28 |
| Compound 4 | 0.26 |
| Compound 5 | 0.071 |
| Compound 6 | 0.48 |
| Compound 7 | 0.033 |
| Compound 8 | 0.03 |
| Compound 9 | 0.14 |
| Compound 10 | 0.031 |
| Compound 10f | 0.037 |
| Compound 11 | 0.045 |
| Compound 12 | 0.29 |
| Compound 13 | 0.037 |
| Compound 14 | 0.034 |
| Compound 15 | 0.03 |
| Compound 16 | 0.31 |
| Compound 17 | 0.27 |
| Compound 18 | 0.019 |
| Compound 19 | 0.032 |
| Compound 20 (control compound) | >10 |
| Compound 21 | 3.37 |
| Compound 22 | 2.18 |

Example 2

Analgesic Activity Test by PGF$_2$α-Induced Allodynia Model Method

To each male ddY mouse, each test compound or the vehicle was subcutaneously administered in an administration volume of 0.1 mL/10 g body weight. Thirty minutes later, PGF2α was intrathecally administered at a dose of 1 μg/mouse in an administration volume of 4 μL/mouse, thereby inducing allodynia. The allodynia was evaluated by scoring the response of each animal when both sides of the body were stroked with a paintbrush according to the following criteria:

Score 0: no response
Score 1: slightly vocalized or disliked the stroking and escaped.
Score 2: loudly vocalized or disliked the stroking and ran about trying to shun, or quickly escaped or flicked.

The evaluation was repeated for 40 minutes with 5 minutes intervals.

The results are shown in FIGS. 1 to 4.

Example 3

Analgesic Activity Test by Rat Chung Model Method

Figure 5:
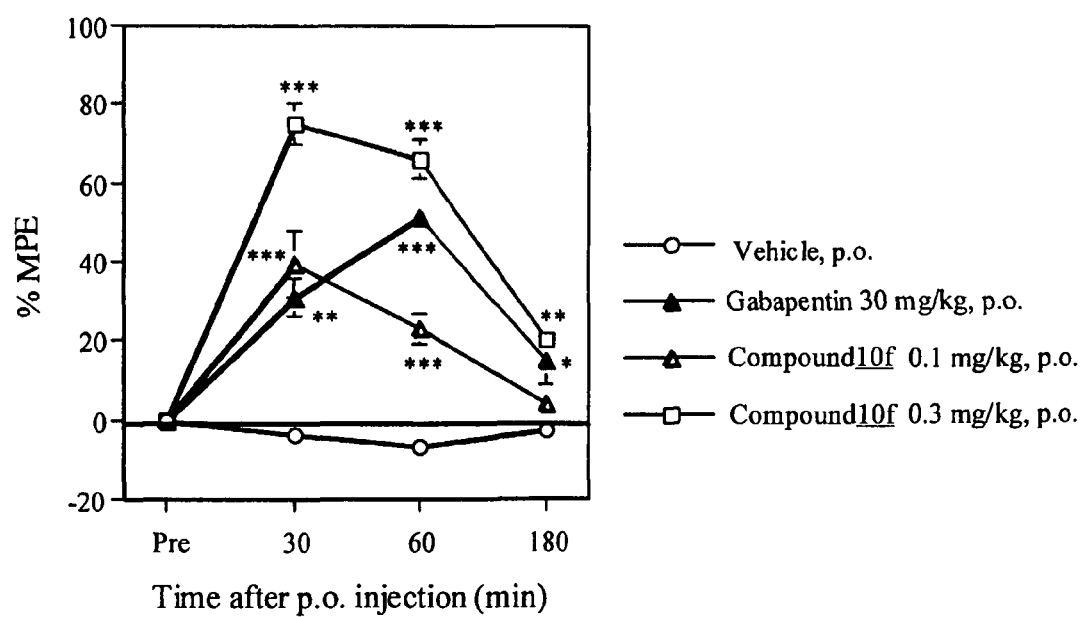
FIG. 5 shows the results of the experiment for confirming the analgesic activity of Compound 10f, by the Chung model method. Each group consisted of 6 rats (n=6). *: P<0.001, : P<0.01, *P<0.05 vs. vehicle-treated group (multiple paired t test corrected with Dunnett's method).

Male SD rats of 7 weeks old were used. Rat Chung model animals were purchased from Japan SLC (the nerve innervating the left hind limb of each rat was ligated when the rat was 6 weeks old). One week after the nerve-ligation treatment or later, the analgesic activity of each of the test compounds and the vehicle was evaluated by the Dixson's Up-Down method (Chaplan S R et al., Journal Neuroscience Methods, 1994, Vol. 53, pp. 55-63) using a filament (North Coast Medical Inc. CA, USA) which exerted a pressure of 0.407, 0.692, 1.202, 2.041, 3.630, 5.495, 8.511 or 15.136 g. The both plantar hind paws were pressed with the filament for 8 seconds (von Frey test). During this stimulation with the filament, if the rat showed avoidance response (raised, tapped or licked the leg(s)), the rat was scored as "responded" (X), and if the rat did not show any avoidance response, the rat was scored as "non-responded" (○). Before the administration of the drug, von Frey test was conducted to obtain the Pre value, and then each drug was orally administered. The von Frey test was performed at 30 minutes, 60 minutes and 180 minutes, respectively, after the drug administration, and % MPE (% Max Possible Effect=(Threshold weight value after the drug administration−Pre Value)/(Cutoff weight (15.00 g)−Pre Value), Each Value: Calculated by the method according to the literature (Chaplan S R et al., Journal Neuroscience Methods, 1994, Vol. 53, p. 55-63)) was determined. The % MPE was employed as an index of analgesic activity. The results are shown in FIG. 5.

Example 4

Analgesic Activity Test by Mouse Seltzer Model Method

Figure 6:
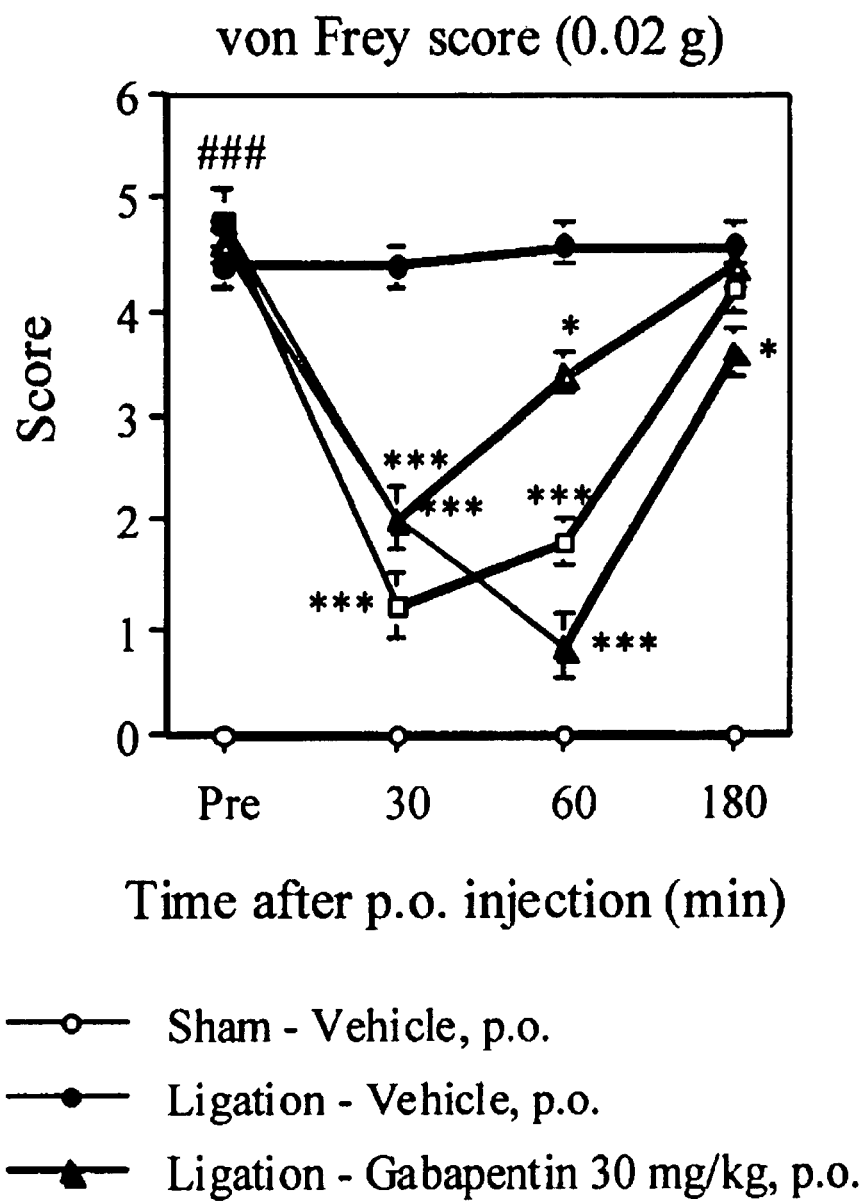
FIG. 6 shows the results of the experiment for confirming the analgesic activity of Compound Gabapentin, by the Seltzer model method. Each group consisted of 5 mice (n=5). ###: P<0.001 vs. sham-vehicle-treated group (student's t test or Welch's test) ***: P<0.001, *: P<0.05 vs. ligation-vehicle-treated group (multiple paired t test corrected with Dunnett's method).
Figure 7:
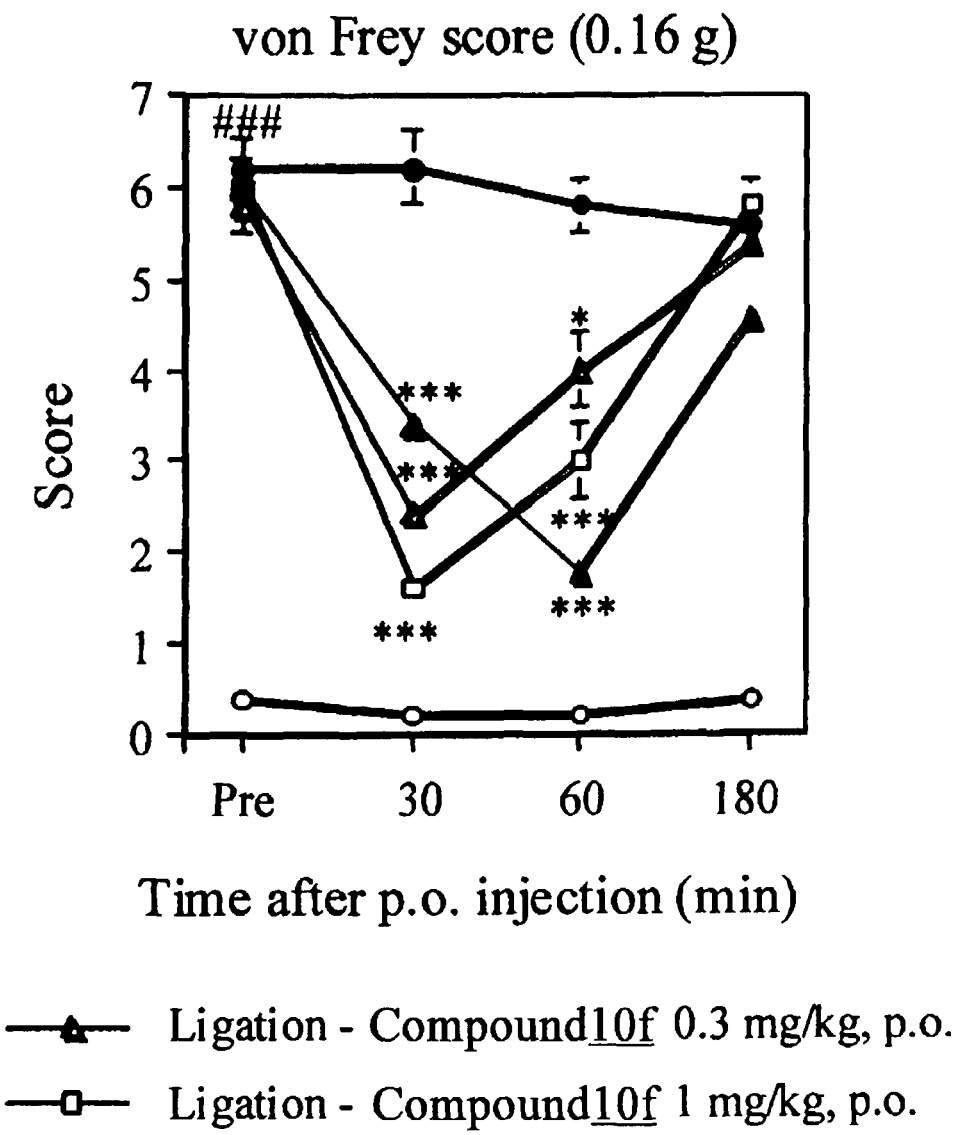
FIG. 7 shows the results of the experiment for confirming the analgesic activity of Compound 10f, by the Seltzer model method. Each group consisted of 5 mice (n=5). ###: P<0.001 vs. sham-vehicle-treated group (student's t test or Welch's test) ***: P<0.001, *: P<0.05 vs. ligation-vehicle-treated group (multiple paired t test corrected with Dunnett's method).

Male ICR mice of 5 weeks old were used. After anesthetizing each mouse with pentobarbital, the sciatic nerve at the femoral region of the right hind limb was exposed, and the sciatic nerve was triply ligated tightly such that only half thickness thereof was pressed with silk suture of 8-0 (USP standard: NATSUME SEISAKUSHO) under microscope. On the other hand, the mice each of which sciatic nerve was exposed but not ligated were used as shams. One week after the nerve-ligation treatment, using a filament (North Coast Medical, Inc. CA, USA) which exerted a pressure of 0.02 g or 0.16 g, the both plantar hind paws were pressed with the filament 3 times for 3 seconds/time with an interval of 3 seconds (von Frey test). The escape behavior during this trial was scored (0: no response, 1: showed slow and slight escape behavior in response to the stimulation, 2: showed quick escape behavior without flinching or licking, 3: showed quick escape behavior with flinching or licking), and the total of the scores obtained in the triplicate pressing trial were used as the indices of the pain. Before the administration of the drug, von Frey test was conducted to obtain the Pre value, and then each drug was orally administered. The von Frey test was performed at 30 minutes, 60 minutes and 180 minutes, respectively, from the drug administration, and the actions of the drugs were evaluated. The results are shown in FIGS. 6 and 7.

Example 5

Figure 8:
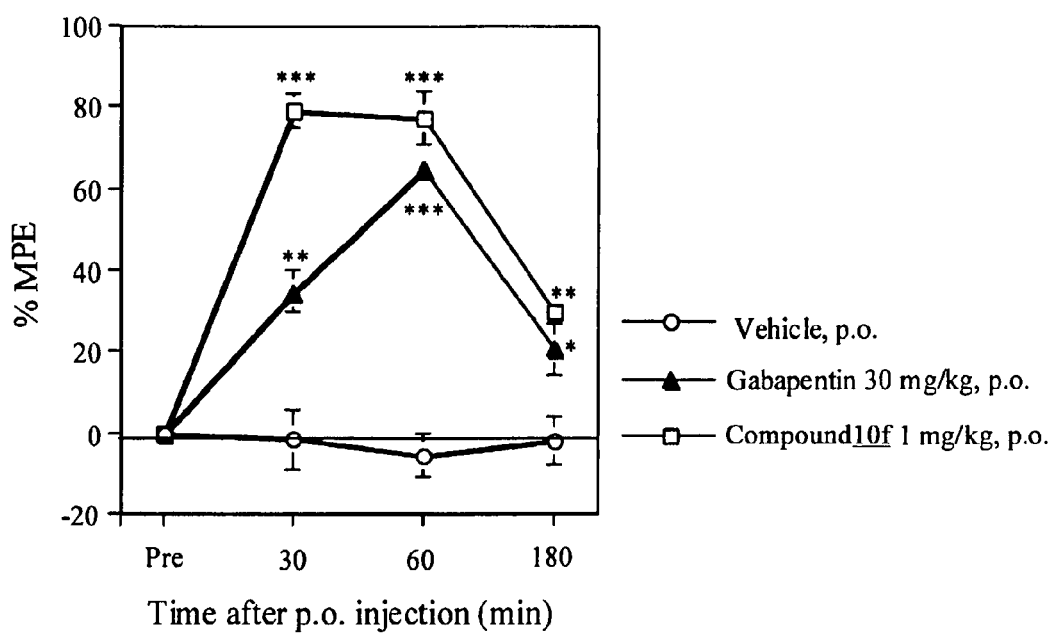
FIG. 8 shows the results of the experiment for confirming the analgesic activity of Compound 10f, by the diabetic induced neuropathic pain model method. Each group consisted of 4 rats (n=4). *: P<0.001, : P<0.01, *P<0.05 vs. vehicle-treated group (multiple paired t test corrected with Dunnett's method).

Analgesic Activity Test by Neurogenic Pain Model Method Using Diabetes-Induced Rats Male SD rats of 10 weeks old were used. Diabetes-induced rats were purchased from Japan SLC (at 6 weeks old, 50 mg/kg of Streptozotocin (STZ) was intraperitoneally administered once). Three weeks after the administration of STZ, blood glucose level was determined with a precision Q•I•D blood glucose meter, and those rats in which the blood glucose levels were not less than 200 mg/dL were judged as diabetes-induced rats. Four weeks after the administration of STZ, the analgesic activity of each of the test compounds and the vehicle was evaluated by the Dixson's Up-Down method (Chaplan S R et al., Journal Neuroscience Methods, 1994, Vol. 53, pp. 55-63) using a filament (North Coast Medical Inc. CA, USA) which exerted a pressure of 0.407, 0.692, 1.202, 2.041, 3.630, 5.495, 8.511 or 15.136 g. The both plantar hind paws were pressed with the filament for 8 seconds (von Frey test). During this stimulation with the filament, if the rat showed avoidance response (raised, tapped or licked the leg(s)), the rat was scored as "responded" (X), and if the rat did not show any avoidance response, the rat was scored as "non-responded" (○). Before administration of the drug, von Frey test was conducted to obtain the Pre value, and then each drug was orally administered. The von Frey test was performed at 30 minutes, 60 minutes and 180 minutes, respectively, after the drug administration, and % MPE was determined. The % MPE was employed as an index of analgesic activity. The results are shown in FIG. 8.

Example 6

Evaluation of Activity to Relieve Cystalgia Caused by Hyperextension of Bladder Using Myoelectric Activity of External Oblique Abdominal Muscle as Index The activity of Compound 10f to relieve cystalgia was evaluated using the myoelectric activity of external oblique abdominal muscle in hyperextension of bladder of anesthetized rats as an index of the cystalgia. In the experiments, 14 to 15-week old female Sprague-Dayley rats (CLEA Japan, Inc.) weighing 300 to 360 g were used.

Under halothane (2.5-4%) anesthesia, a polyethylene catheter (PE-50) for cystometry was inserted into the bladder transurethrally. Further, a polyethylene catheter (PE-100) for filling physiological saline was inserted into the bladder from the apex of bladder dome. Each catheter was tightly ligated so that physiological saline does not leak from the site of insertion. A catheter for drug administration was indwelled in the femoral vein. The skin in the lateral ventral part was incised and a bipolar electrode for electromyographic measurement was inserted into the external oblique abdominal muscle and indwelled therein. A reservoir preliminarily filled with physiological saline was connected to the catheter indwelled in the bladder and held at a prescribed height to extend the bladder. The extension stimulus was continued for 20 seconds. In cases where the stimulation is repeatedly given, the interval between stimulation was 3 minutes. A bipolar electrode (needle electrode for electroencephalography, NIHON KOHDEN) was connected to an electromyograph amplifier (EMG100C, Biopac Systems), and a high cut filter (5 kHz) and low cut filter (100 Hz) were applied. Thereafter, the signals were taken into an AD converter (MP-150WSW, Biopac Systems) and into a computer at 1 kHz, and the myoelectric activity was recorded using the special software (Acq-Knowledge 3.8.1, Biopac Systems). The intravesical pressure was measured using a pressure transducer (AP641G, NIHON KOHDEN) and a general purpose amplifier (DA100C, Biopac Systems). The halothane level was adjusted such that a stable myoelectric activity was obtained by extension at a pressure of 50 cmH$_2$O, and then the drug was intravenously administered. Thereafter, hyperextension of bladder was repeated for at least 20 minutes.

The drug was dissolved in aqueous 5% xylitol-0.02% citric acid solution, and the administration volume was 0.5 mL/kg. The mean of the number of spikes during the twice hyperextension of bladder immediately before the drug administration was defined as the value before drug administration. Taking the value before the drug administration as 100%, the change in the number of spikes after administration of the drug was normalized. The mean of the change in the number of spikes by the consecutive three times hyperextension carried out immediately before or after 15-minutes time point from the drug administration was calculated, and the drug effect was analyzed by Williams test.

As shown in Table 7, Compound 10f dose-dependently and significantly inhibited the myoelectric activity. The minimum effective dose was 0.01 mg/kg.

TABLE 8

Action of Compound 10f on Myoelectric Activity of External Oblique Abdominal Muscle by Hyperextension of Bladder

| Drug | Dose (mg/kg, iv) | Number of animals | Rate of Inhibition of Myoelectric Activity (Number of Spikes) of External Oblique Abdominal Muscle (vs. before administration, %) |
|---|---|---|---|
| Vehicle |  | 9 | −19.4 ± 19.9 |
| Compound A | 0.003 | 6 | 5.9 ± 11.5 |
|  | 0.01 | 6 | 42.4 ± 21.1* |
|  | 0.03 | 7 | 64.3 ± 17.2* |

The data represent mean ± standard error.
*P < 0.025 (significance vs. control group treated with vehicle, Williams test)

INDUSTRIAL AVAILABILITY

The analgesic has a very high analgesic effect, may be applied to various types of pain ranging from acute pain to chronic pain.

The invention claimed is:

1. A method for relieving or allaying pain, comprising administering an effective amount of one or more morphinan derivatives having a nitrogen-containing heterocyclic group represented by Formula (I):

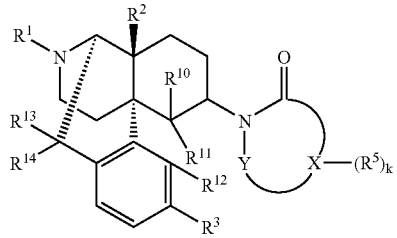
(I)

wherein $R^1$ is $C_4$-$C_7$ cycloalkylalkyl;
$R^2$ and $R^3$ are hydroxy;
—X— is $C_2$ alkylene constituting a part of the ring structure;
Y represents —C(=O)—;
k is 2;
$R^5$s are substituents in the number of k on a cyclic structure, which are two $R^5$s bound to adjacent carbon atoms, respectively, cooperatively form benzo or cyclohexano, each of these rings formed with said two $R^5$s bound to adjacent carbon atoms being non-substituted or substituted with 1 or more $R^6$s;

$R^6$(s) independently is (are) fluoro or $C_1$-$C_5$ alkyl;
$R^{10}$ is hydrogen;
$R^{11}$ and $R^{12}$ are bound to form —O—;
$R^{13}$ and $R^{14}$ are hydrogen or a pharmaceutically acceptable acid addition salt thereof.

2. The method according to claim 1, wherein the pain is neuropathic pain

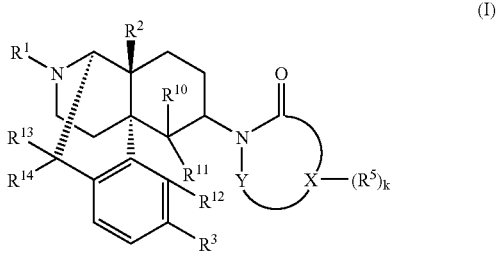
(I)

3. The method according to claim 1, wherein the rain is diabetic neuralgia

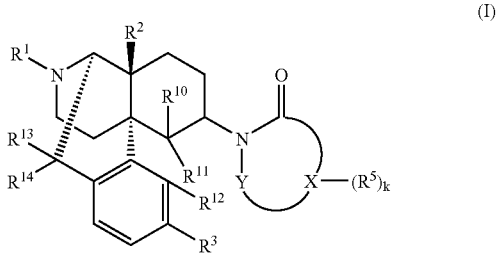
(I)

4. The method according to claim 1, wherein the pain is cystalgia

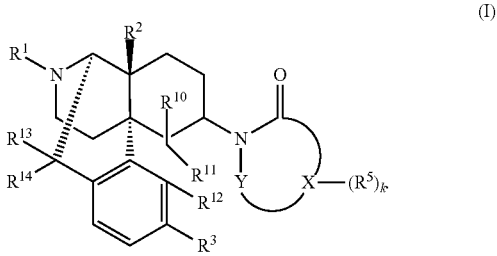
(I)

5. The method according to claim 1, wherein in said Formula (I), $R^1$ is cyclopropylmethyl.

* * * * *

UNITED STATES PATENT AND TRADEMARK OFFICE
CERTIFICATE OF CORRECTION

| | | |
|---|---|---|
| PATENT NO. | : 8,470,845 B2 | Page 1 of 1 |
| APPLICATION NO. | : 11/667136 | |
| DATED | : June 25, 2013 | |
| INVENTOR(S) | : Izumimoto et al. | |

It is certified that error appears in the above-identified patent and that said Letters Patent is hereby corrected as shown below:

On the Title Page of the Patent

At (86), please change "May 4, 2007" to -- June 21, 2007 --.

In the Specification

In Column 32

At line 22, claim 3, please change "rain" to -- pain --.

Signed and Sealed this
Seventeenth Day of June, 2014

Michelle K. Lee
*Deputy Director of the United States Patent and Trademark Office*